(12) United States Patent
George et al.

(10) Patent No.: US 9,067,989 B2
(45) Date of Patent: Jun. 30, 2015

(54) EOTAXIN-2 (CCL24) INHIBITORS IN INFLAMMATORY, AUTOIMMUNE, AND CARDIOVASCULAR DISORDERS

(75) Inventors: Jacob George, Tel-Aviv (IL); Gad Keren, Kiryat Ono (IL)

(73) Assignee: THE MEDICAL RESEARCH, INFRASTRUCTURE, AND HEALTH SERVICES FUND OF THE TEL AVIV MEDICAL CENTER, Tel Aviv (IL)

( * ) Notice: Subject to any disclaimer, the term of this patent is extended or adjusted under 35 U.S.C. 154(b) by 67 days.

(21) Appl. No.: 13/146,711

(22) PCT Filed: Jan. 28, 2010

(86) PCT No.: PCT/IL2010/000073
§ 371 (c)(1),
(2), (4) Date: Aug. 8, 2011

(87) PCT Pub. No.: WO2010/086854
PCT Pub. Date: Aug. 5, 2010

(65) Prior Publication Data
US 2011/0280832 A1 Nov. 17, 2011

Related U.S. Application Data

(60) Provisional application No. 61/202,089, filed on Jan. 28, 2009, provisional application No. 61/244,530, filed on Sep. 22, 2009.

(51) Int. Cl.
| | |
|---|---|
| *A61K 39/395* | (2006.01) |
| *A61K 38/13* | (2006.01) |
| *A61K 38/21* | (2006.01) |
| *C07K 16/24* | (2006.01) |
| *A61K 39/00* | (2006.01) |

(52) U.S. Cl.
CPC ................ *C07K 16/24* (2013.01); *A61K 38/13* (2013.01); *A61K 38/215* (2013.01); *A61K 2039/505* (2013.01)

(58) Field of Classification Search
CPC ..... C07K 16/24; A61K 38/13; A61K 38/215; A61K 2039/505
See application file for complete search history.

(56) References Cited

U.S. PATENT DOCUMENTS

2007/0190055 A1* 8/2007 Ambati ...................... 424/145.1

FOREIGN PATENT DOCUMENTS

| WO | 97/00960 A1 | 1/1997 |
| WO | 98/44118 A1 | 10/1998 |
| WO | 2006/093932 A2 | 9/2006 |

OTHER PUBLICATIONS

Keystone et al., Certolizumab pegol plus methotrexate is significantly more effective than placebo plus methotrexate in active rheumatoid arthritis: findings of a fifty-two-week, phase III, multicenter, randomized, double-blind, placebo-controlled, parallel-group study. Arthritis Rheum. 58(11):3319-3329, 2008.*
Arend, "Physiology of Cytokine Pathways in Rheumatoid Arthritis", Arthritis Care & Research, vol. 45, pp. 101-106, (2001).
Berger, et al., "CXC and CC Chemokine Receptors on Coronary and Brain Endothelia", Molecular Medicine, vol. 5, pp. 795-805, (1999).
Bocchino, et al., "Eotaxin and CCR3 are up-regulated in exacerbations of chronic bronchitis", Allergy, vol. 57, pp. 17-22, (2002).
Charo, et al., "Chemokines in the Pathogenesis of Vascular Disease", Circ Res., vol. 95, pp. 858-866, (2004).
Cheng, et al., "Eotaxin/CCL11 Suppresses IL-8/CXCL8 Secretion from Human Dermal Microvascular Endothelial Cells", J Immunol, vol. 168, pp. 2887-2894, (2002).
Delovitch, et al., "The Nonobese Diabetic Mouse as a Model of Autoimmune Diabetes: Immune Dysregulation Gets the NOD", Immunity, vol. 7, pp. 727-738, (1997).
Economou, et al., "Chemokines in patients with ischaemic heart disease and the effect of coronary angioplasty", International Journal of Cardiology, vol. 80, pp. 55-60, (2001).
Emanuele, et al., "Association of plasma eotaxin levels with the presence and extent of angiographic coronary artery disease", Atherosclerosis, vol. 186, pp. 140-145, (2006).
Firestein, "Evolving concepts of rheumatoid arthritis", Nature, vol. 423, pp. 356-361, (2003).
Forssmann, et al., "Eotaxin-2, a Novel CC Chemokine that Is Selective for the Chemokine Receptor CCR3, and Acts Like Eotaxin on Human Eosinophil and Basophil Leukocytes", J. Exp. Med., vol. 185, No. 12, pp. 2171-2176, (1997).
Garcia, et al., "New Chemokine Targets for Asthma Therapy", Current Allergy and Asthma Reports, vol. 5, pp. 155-160, (2005).
George, et al., "Induction of Early Atherosclerosis in LDL-Receptor-Deficient Mice Immunized With β2-Glycoprotein I", Circulation, vol. 98, pp. 1108-1115, (1998).
Guglielmotti, et al., "Amelioration of rat adjuvant arthritis by therapeutic treatment with bindarit, an inhibitor of MCP-1 and TNF-αproduction", Inflamm. res., vol. 51, pp. 252-258, (2002).
Haas, et al., "Chemokine Receptor Expression in Rat Adjuvant-Induced Arthritis", Arthritis & Rheumatism, vol. 52, No. 12, pp. 3718-3730, (2005).
Haley, et al., "Overexpression of Eotaxin and the CCR3 Receptor in Human Atherosclerosis: Using Genomic Technology to Identify a Potential Novel Pathway of Vascular Inflammation", Circulation, vol. 102, pp. 2185-2189, (2000).

(Continued)

*Primary Examiner* — Ruixiang Li
(74) *Attorney, Agent, or Firm* — Vorys, Sater, Seymour and Pease LLP; Susanne M. Hopkins

(57) ABSTRACT

The presently described subject matter is based on the finding that inhibition of eotaxin-2 by polyclonal or monoclonal antibodies, has a significant protective effect in animal models of inflammatory diseases such as rheumatoid arthritis, experimental autoimmune encephalomyelitis (EAE), colitis, diabetes, and atherosclerosis. Thus, provided are pharmaceutical compositions including specific anti-eotaxin 2 antibodies for use alone or in combination with other therapeutic agents in the treatment of inflammatory, autoimmune and cardiovascular diseases. Also provided are specific anti-eotaxin-2 monoclonal antibodies, and methods of treatment utilizing such antibodies.

18 Claims, 20 Drawing Sheets

(56) References Cited

OTHER PUBLICATIONS

Haringman, et al., "Chemokine and chemokine receptor expression in paired peripheral blood mononuclear cells and synovial tissue of patients with rheumatoid arthritis, osteoarthritis, and reactive arthritis", Ann Rheum Dis, vol. 65, pp. 294-300, (2006).

Jose, et al', "Eotaxin: A Potent Eosinophil Chemoattractant Cytokine Detected in a Guinea Pig Model of Allergic Airways Inflammation", J. Exp. Med., vol. 179, pp. 881-887, (1994).

Kitaura, et al., "Molecular Cloning of Human Eotaxin, an Eosinophil-selective CC Chemokine, and Identification of a Specific Eosinophil Eotaxin Receptor, CC Chemokine Receptor 3", The Journal of Biological Chemistry, vol. 271, No. 13, pp. 7725-7730, (1996).

Kodali, et al., "CCL11 (Eotaxin) Induces CCR3-Dependent Smooth Muscle Cell Migration", Arterioscler Thromb Vasc Biol., vol. 24, pp. 1211-1216, (2004).

Mendel, et al., "A myelin oligodendrocyte glycoprotein peptide induces typical chronic experimental autoimmune encephalomyelitis in H-2b mice: fine specificity and T cell receptor Vβ expression of encephalitogenic T cells", Eur. J. Immunol., vol. 25, pp. 1951-1959, (1995).

Naghavi, et al., "From Vulnerable Plaque to Vulnerable Patient: A Call for New Definitions and Risk Assessment Strategies: Part I", Circulation, vol. 108, pp. 1664-1672, (2003).

Naghavi, et al., "From Vulnerable Plaque to Vulnerable Patient: A Call for New Definitions and Risk Assessment Strategies: Part II", Circulation, vol. 108, pp. 1772-1778, (2003).

Ponath, et al., "Cloning of the Human Eosinophil Chemoattractant, Eotaxin", J. Clin. Invest., vol. 97, No. 3, pp. 604-612, (1996).

Rådinger, et al., "Eotaxin-2 regulates newly produced and CD34+ airway eosinophils after allergen exposure", Allergy Clin Immunol, vol. 113, pp. 1109-1116, (2004).

Romagnani, et al., "Cell cycle-dependent expression of CXC chemokine receptor 3 by endothelial cells mediates angiostatic activity", J. Clin. Invest., vol. 107, No. 1, pp. 53-63, (2001).

Salcedo, et al., "Differential expression and responsiveness of chemokine receptors (CXCR1-3) by human microvascular endothelial cells and umbilical vein endothelial cells", FASEB J., vol. 14, pp. 2055-2064, (2000).

Salcedo, et al., "Eotaxin (CCL11) Induces In Vivo Angiogenic Responses by Human CCR3+ Endothelial Cells", J Immunol, vol. 166, pp. 7571-7578, (2001).

Sheikine, et al., "Chemokines as Potential Therapeutic Targets in Atherosclerosis", Current Drug Targets, vol. 7, pp. 13-27, (2006).

Sheikine, et al., "Influence of eotaxin 67G>A polymorphism on plasma eotaxin concentrations in myocardial infarction survivors and healthy controls", Atherosclerosis, vol. 189, pp. 458-463, (2006).

Simpson, et al., "Expression of the β-chemokine receptors CCR2, CCR3 and CCR5 in multiple sclerosis central nervous system tissue", Journal of Neuroimmunology, vol. 108, pp. 192-200, (2000).

Viola, et al., "Chemokines and Their Receptors: Drug Targets in Immunity and Inflammation", Annu. Rev. Pharmacol. Toxicol., vol. 48, pp. 171-197, (2008).

Zargari, et al., "Relationship between the clinical scoring and demyelination in central nervous system with total antioxidant capacity of plasma during experimental autoimmune encephalomyelitis development in mice", Neuroscience Letters, vol. 412, pp. 24-28, (2007).

Zimmerman, et al., "Chemokines and Chemokine Receptors in Mucosal Homeostasis at the Intestinal Epithelial Barrier in Inflammatory Bowel Disease", Inflamm Bowel Dis, vol. 14, No. 7, pp. 1000-1011, (2008).

The International Search Report for International Application No. PCT/IL2010/000073, two pages, mailed on May 18, 2010.

Fichtner-Feigl et al., "Treatment of murine Th1- and Th2-mediated inflammatory bowel disease with NF-κB decoy oligonucleotides", The Journal of Clinical Investigation, vol. 115, No. 11, pp. 3057-3071, (2005).

Sun et al., "Inhibition of Th2-Mediated Allergic Airway Inflammatory Disease by CD137 Costimulation", J Immunol, vol. 177, pp. 814-821, (2006).

Zhu et al., "Acidic Mammalian Chitinase in Asthmatic Th2 Inflammation and IL-13 Pathway Activation", Science, vol. 304, pp. 1678-1682, (2004).

Fu, et al., "Establishment of human lymphocyte cell line secreting monoclonal antibodies against Rhesus(D) antigen and sequence analysis of a human monoclonal anti-D Fab fragment", Chinese Journal of Pathophysiology, vol. 18, No. 3, pp. 276-281, Mar. 30, 2002. (Abstract attached).

* cited by examiner

MPO activity in colitis mice

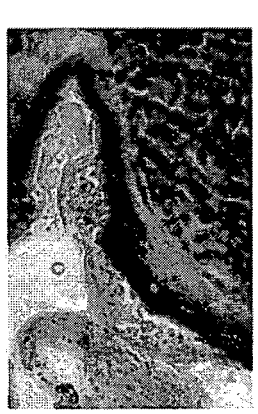
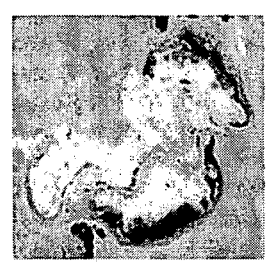

SEQUENCE LISTING

```
<160> NUMBER OF SEQ IDS NOS: 17

<210> SEQ ID NO 1
<211> LENGTH: 452
<212> TYPE: DNA
<213> ORGANISM: Mus musculus
<220> FEATURE:
<221> NAME/KEY: misc_feature
<222> LOCATION: (1)..(26)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (59)..(59)
```

```
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (448)..(448)
<223> OTHER INFORMATION: n is a, c, g, or t

<400> SEQUENCE: 1
nnnnnnnnnn nnnnnnnnnn nnnnnnggqc agcagancog gggcngngga tagacagang    60
ggggnngncg ttttggctga ggagacggtg actgaggttc cttgacccca gttgtccata   120
gcgtagctac taccgtagga atgacttgca cagaaatatg tagccgtgtc ctcatttctg   180
aggttgttga tctgcaaata ggcagtgctg gcagaggttt ccaaagagag ggcaaaccgt   240
cccttgaagt catcagtata tgttggctct ccattgtagg tgttgatcca gcccatccac   300
tttaaaccct ttcctggagc ctgctttacc cagttcattc cagagtttgt gaagggatac   360
ccagaagccc tgcaggagat cttgactgtg tctccaggct tcttcagctc angtccagac   420
tgcaccaact ggatctgggc catggccngc ta                                 452

<210> SEQ ID NO 2
<211> LENGTH: 294
<212> TYPE: DNA
<213> ORGANISM: Mus musculus
<220> FEATURE:
<221> NAME/KEY: misc_feature
<222> LOCATION: (1)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(40)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (75)..(76)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (89)..(92)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
```

```
<222> LOCATION: (100)..(101)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (115)..(118)
<223> OTHER INFORMATION: n is a, c, g, or t
<220> FEATURE:
<221> NAME/KEY: misc_feature
<222> LOCATION: (120)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (147)..(149)
<223> OTHER INFORMATION: n is a, c, g, or t
<220> FEATURE:
<221> NAME/KEY: misc_feature
<222> LOCATION: (151)..(153)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (159)..(161)
<223> OTHER INFORMATION: n is a, c, g, or t
<220> FEATURE:
<221> NAME/KEY: misc_feature
<222> LOCATION: (165)..(166)
<223> OTHER INFORMATION: n is a, c, g, or t
<220> FEATURE:
<221> NAME/KEY: misc_feature
<222> LOCATION: (171)..(177)
<223> OTHER INFORMATION: n is a, c, g, or t
<220> FEATURE:
<221> NAME/KEY: misc_feature
<222> LOCATION: (179)..(182)
<223> OTHER INFORMATION: n is a, c, g, or t
<220> FEATURE:
<221> NAME/KEY: misc_feature
<222> LOCATION: (185)..(189)
<223> OTHER INFORMATION: n is a, c, g, or t
<220> FEATURE:
```

```
<221> NAME/KEY: misc_feature
<222> LOCATION: (193)..(194)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (203)..(206)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (211)..(213)
<223> OTHER INFORMATION: n is a, c, g, or t
<220> FEATURE:
<221> NAME/KEY: misc_feature
<222> LOCATION: (218)..(218)
<223> OTHER INFORMATION: n is a, c, g, or t
<220> FEATURE:
<221> NAME/KEY: misc_feature
<222> LOCATION: (220)..(221)
<223> OTHER INFORMATION: n is a, c, g, or t
<220> FEATURE:
<221> NAME/KEY: misc_feature
<222> LOCATION: (223)..(225)
<223> OTHER INFORMATION: n is a, c, g, or t
<220> FEATURE:
<221> NAME/KEY: misc_feature
<222> LOCATION: (227)..(231)
<223> OTHER INFORMATION: n is a, c, g, or t
<220> FEATURE:
<221> NAME/KEY: misc_feature
<222> LOCATION: (236)..(240)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (256)..(258)
<223> OTHER INFORMATION: n is a, c, g, or t
<220> FEATURE:
<221> NAME/KEY: misc_feature
<222> LOCATION: (261)..(266)
<223> OTHER INFORMATION: n is a, c, g, or t
<220> FEATURE:
<221> NAME/KEY: misc_feature
<222> LOCATION: (273)..(274)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t

<400> SEQUENCE: 2
nnnnnnnnnn nnnnnnnnnn ntnntngnnn nnnnnnnnnn gggccaatgg nngaggacgc    60
```

-continued

```
ggatggggt  gtcgnngtgc  cttngtcgnn  nnctnnttgn  ncancntcna  cnncnnnnan    120
nnnanngnnn  nntgnaanan  ngatggnnnt  nnncnacann  ntggnntcct  nnnnnnntnn    180
nntgnnnnng  acnncanana  cannnncnac  nnnatgancn  ncnnncnnnn  nttgannnnn    240
gncnantatg  aacnannnaa  nnnnnntacc  tgnnangcca  ctcacaagac  atca          294
```

<210> SEQ ID NO 3
<211> LENGTH: 455
<212> TYPE: DNA
<213> ORGANISM: Mus musculus
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (17)..(26)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (454)..(455)
<223> OTHER INFORMATION: n is a, c, g, or t

<400> SEQUENCE: 3

```
nnnnnnnnnn  nnnggnnnn  nnnnnngggc  agcagntcca  ggggccagng  gatagacaga     60
ngggggngtc  gttttggctg  aggagacggt  gactgaggtt  ccttgacccc  agttgtccat   120
agcgtagcta  ctaccgtagg  aatgacttgc  acagaaatat  gtagccgtgt  cctcatttct   180
gaggttgttg  atctgcaaat  aggcagtgct  ggcagaggtt  ccaaagaga  gggcaaaccg    240 tcccttgaag  tcatcagtat  atgttggctc  tccattgtag  gtgttgatcc  agcccatcca   300
ctttaaaccc  tttcctggag  cctgctttac  ccagttcatt  ccagagtttg  tgaagggata   360
cccagaagcc  ctgcaggaga  tcttgactgt  gtctccaggc  ttcttcagct  caggtccaga   420
ctgcaccaac  tggatctggg  ccatggccgg  ctann                                455
```

<210> SEQ ID NO 4
<211> LENGTH: 293
<212> TYPE: DNA
<213> ORGANISM: Mus musculus
<220> FEATURE:
<221> NAME/KEY: misc_feature
<222> LOCATION: (1)..(25)
<223> OTHER INFORMATION: n is a, c, g, or t
<220> FEATURE:
<221> NAME/KEY: misc_feature
<222> LOCATION: (27)..(38)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:

```
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (123)..(124)
<223> OTHER INFORMATION: n is a, c, g, or t
<220> FEATURE:
<221> NAME/KEY: misc_feature
<222> LOCATION: (127)..(130)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (236)..(239)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
```

<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (259)..(262)
<223> OTHER INFORMATION: n is a, c, g, or t
<220> FEATURE:
<221> NAME/KEY: misc_feature
<222> LOCATION: (264)..(265)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t

<400> SEQUENCE: 4
nnnnnnnnnn nnnnnnnnnn nnnnngnnnn nnnnnnnngg gccaatggnn gaggacgcgg      60 atggggtgt cgnngtgcct tngtcgngtg cttnttgaac aacttctacc ccnnanacnt      120
nanngtnnnn tggaanattg atggcngtga acgacaaaat ggcgtcctga acanttggac    180
tgatccanga cagcaaanac ancncctaca gcatgagcag caccctcacg ttgacnnnng   240
acnantntga acgacgtann nncnntacct gtnangccac tcacaagaca tca           293

<210> SEQ ID NO 5
<211> LENGTH: 456
<212> TYPE: DNA
<213> ORGANISM: Mus musculus
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (17)..(26)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t

<400> SEQUENCE: 5
nnnnnnnnnn nnnnggnnnn nnnnnngggc agcagntcca ggggccagnn ggatagacag      60 anggggngn cgttttggct gaggagacgg tgactgaggt tccttgaccc cagttgtcca     120
tagcgtagct actaccgtag gaatgacttg cacagaaata tgtagccgtg tcctcatttc   180

```
tgaggttgtt gatctgcaaa taggcagtgc tggcagaggt ttccaaagag agggcaaacc    240
gtcccttgaa gtcatcagta tatgttggct ctccattgta ggtgttgatc cagcccatcc    300
actttaaacc ctttcctgga gcctgcttta cccagttcat tccagagttt gtgaagggat    360
acccagaagc cctgcaggag atcttgactg tgtctccagg cttcttcagc tcaggtccag    420
actgcaccaa ctggatctgg gccatggccg gctann                              456
```

```
<210> SEQ ID NO 6
<211> LENGTH: 293
<212> TYPE: DNA
<213> ORGANISM: Mus musculus
<220> FEATURE:
<221> NAME/KEY: misc_feature
<222> LOCATION: (1)..(25)
<223> OTHER INFORMATION: n is a, c, g, or t
<220> FEATURE:
<221> NAME/KEY: misc_feature
<222> LOCATION: (27)..(38)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (123)..(124)
<223> OTHER INFORMATION: n is a, c, g, or t
<220> FEATURE:
<221> NAME/KEY: misc_feature
<222> LOCATION: (127)..(130)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
```

<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (236)..(239)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (259)..(262)
<223> OTHER INFORMATION: n is a, c, g, or t
<220> FEATURE:
<221> NAME/KEY: misc_feature
<222> LOCATION: (264)..(265)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t

<400> SEQUENCE: 6

```
nnnnnnnnnn nnnnnnnnnn nnnnngnnnn nnnnnnnngg gcctttggnn gaggacgcgg      60
atgggggtgt ccnngtgcct tngtcgngtg cttnttgaac aacttctacc ccnnanacnt     120
nanngtnnnn tggaanattg atggcngtga acgacaaaat ggcgtcctga acanttggac    180
tgatccanga cagcaaatac ancncctaca gcatgagcag caccctcacg ttgacnnnng    240
acnantntga acgacgtann nncnntacct gtnangccac tcacaagaca tca           293
```

<210> SEQ ID NO 7
<211> LENGTH: 78
<212> TYPE: DNA
<213> ORGANISM: Mus musculus

<400> SEQUENCE: 7

```
cgaagagaca gtgaccagag tcccttggcc ccagtaagca aagctattac cgaaggtaca     60
gtaatacacg gccgtgtc                                                   78
```

<210> SEQ ID NO 8
<211> LENGTH: 24
<212> TYPE: DNA
<213> ORGANISM: Mus musculus

<400> SEQUENCE: 8

```
cggggaagta gtccttgacc aggc                                            24
```

```
<210> SEQ ID NO 9
<211> LENGTH: 19
<212> TYPE: DNA
<213> ORGANISM: Mus musculus

<400> SEQUENCE: 9
rrhryybwdm tvacharwc                                                    19

<210> SEQ ID NO 10
<211> LENGTH: 22
<212> TYPE: DNA
<213> ORGANISM: Mus musculus

<400> SEQUENCE: 10
gatgtcttgt gagtggcctc ac                                                22

<210> SEQ ID NO 11
<211> LENGTH: 24
<212> TYPE: DNA
<213> ORGANISM: Mus musculus

<400> SEQUENCE: 11
tgggatagaa gttattcagc aggc                                              24

<210> SEQ ID NO 12
<211> LENGTH: 20
<212> TYPE: DNA
<213> ORGANISM: Mus musculus

<400> SEQUENCE: 12
ctgtgcctga cctccagaac                                                   20

<210> SEQ ID NO 13
<211> LENGTH: 20
<212> TYPE: DNA
<213> ORGANISM: Mus musculus

<400> SEQUENCE: 13
ctaaacctcg gtgctattgc                                                   20

<210> SEQ ID NO 14
<211> LENGTH: 24
<212> TYPE: DNA
<213> ORGANISM: Mus musculus

<400> SEQUENCE: 14
cttgggcttg cgacccacgt agta                                              24

<210> SEQ ID NO 15
<211> LENGTH: 26
<212> TYPE: DNA
<213> ORGANISM: Mus musculus

<400> SEQUENCE: 15
agacggaata cagggctttc gattca                                            26

<210> SEQ ID NO 16
<211> LENGTH: 20
<212> TYPE: DNA
<213> ORGANISM: Mus musculus

<400> SEQUENCE: 16
agcccatcac catcttccag                                                   20
```

```
<210> SEQ ID NO 17
<211> LENGTH: 20
<212> TYPE: DNA
<213> ORGANISM: Mus musculus

<400> SEQUENCE: 17
cctgcttcac caccttcttg                                                    20
```

EOTAXIN-2 (CCL24) INHIBITORS IN INFLAMMATORY, AUTOIMMUNE, AND CARDIOVASCULAR DISORDERS

This is a National Phase Application filed under 35 U.S.C. §371 as a national stage of PCT/IL2010/000073, filed on Jan. 28, 2010, an application claiming the benefit under 35 U.S.C. §119(e) of U.S. Provisional Application No. 61/202,089, filed on Jan. 28, 2009, and an application claiming the benefit under 35 U.S.C. §119(e) of U.S. Provisional Application No. 61/244,530, filed on Sep. 22, 2009, the content of each of which is hereby incorporated by reference in its entirety.

FIELD OF INVENTION

The present invention concerns the use of inhibitors of eotaxin-2 (CCL24) in the treatment of inflammatory, autoimmune, and cardiovascular disorders, in particular anti eotaxin-2 polyclonal or monoclonal antibodies.

"The Sequence Listing submitted in text format (.txt) on Jul. 28, 2011, named "SequenceListing.txt", (created on Thursday, Jul. 27, 2011, 15.0 KB), is incorporated herein by reference."

BACKGROUND OF INVENTION

Chemokines are small cytokines which act as chemoattractants for leukocytes, coordinating both homeostatic trafficking of these cells as well as recruiting specific cell populations to sites of inflammation. Chemokine dysregulation is considered to play a part in a wide spectrum of human diseases involving the immune system including inflammation and autoimmunity (1).

The human eotaxin family includes three known cytokines which belong to the CC chemokine family:

Eotaxin 1 (eosinophil chemotactic protein 1, also termed eotaxin or Chemokine (C—C motif) ligand 11 (CCL11)) is known to selectively recruit eosinophils by inducing their chemotaxis and therefore, is implicated in allergic responses.

Eotaxin 2 (eosinophil chemotactic protein 2, also termed Chemokine (C—C motif) ligand 24 (CCL24), myeloid progenitor inhibitory factor 2 (MPIF-2)) is a potent chemo attractant for inflammatory cells including eosinophils (2-4), basophils (4), Th2-type lymphocytes (5) and neutrophils. Eotaxin-2 is expressed in various types of endothelial cells (5-9), and induces angiogenic and migratory responses in endothelial (10) and smooth muscle cells (11).

Eotaxin 3 (eosinophil chemotactic protein 3, Chemokine (C—C motif) ligand 26 (CCL26), Macrophage inflammatory protein 4-alpha (MIP-4-alpha), Thymic stroma chemokine-1 (TSC-1), and IMAC) is chemotactic for eosinophils and basophils.

Eotaxin-2 is only 39% homologous to eotaxin, and the two polypeptides differ almost completely in the NH$_2$-terminal region (12). Eotaxin-2 is located on chromosome 7q11.23 and eotaxin is located on chromosome 17q21.1. The eotaxin-3 gene lies close to the eotaxin-2 gene on chromosome 7 but shares only 33% homology with it. These chemokines bind specifically to the CCR3 receptor. CCR3, the eotaxin receptor, is a 7-transmembrane G protein-coupled receptor which is expressed by eosinophils as well as by a wide array of cell types including macrophages and endothelial cells (13).

WO 97/00960 discloses nucleic acids which encode human eotaxin (CCL11), as well as isolated or recombinant human eotaxin proteins. WO 97/00960 also discloses methods of use of the eotaxin proteins in the recruitment of eosinophils to a particular site or in the treatment of allergic conditions.

CCR3 expression was originally studied in the pathogenesis of asthma and allergy, where it continues to serve as a therapeutic target (14). More recently however, a role for this pathway has emerged in the study of additional inflammatory and autoimmune disorders including inflammatory bowel disease (15), multiple sclerosis (16) and rheumatoid arthritis (RA).

Rheumatoid arthritis (RA) is a common, chronic inflammatory disease, characterized by intense, destructive infiltration of synovial tissue by a broad spectrum of inflammatory cells (17). Multiple cytokines, derived from macrophages and fibroblasts are responsible for the secretion of both cytokines and chemokines in (RA) (18). The accumulation of leukocytes in the joint space leads to secretion of tissue degrading factors, including cytokines and matrix degrading enzymes.

Chemokine inhibition has previously been tested as a therapeutic option in adjuvant induced arthritis, a commonly used animal model of RA (19). Using the same model, CCR3 has been shown to play a role in recruitment of leukocytes to synovial tissue (20). Differential expression of many chemokines and chemokine receptors has also been demonstrated in serum and synovial tissue of RA patients (21).

Inflammation with involvement of cytokines and chemokines is thought to play a pivotal role also in promoting atherosclerotic plaque growth and propensity to destabilize and subsequently rupture (22, 23). Eotaxin/CCL24 receptor (CCR3) is expressed in plaque macrophages (24). A clinical study demonstrated that in a cohort of healthy men, a non-conservative polymorphism in the eotaxin gene has been associated with increased risk for myocardial infarction (25). In a subsequent study, it has been found that increased circulating eotaxin level is associated with the presence of coronary atherosclerosis and ischemia (26, 27).

Atherosclerosis is a process in which fat deposition progresses in the arterial wall leading to progressive narrowing of the lumen. The mature plaque is composed of two basic structures: the lipid core and the fibrous cap. The smaller the lipid core and the thicker the fibrous cap, the more stable the plaque is, meaning that its propensity to rupture and cause myocardial infarction or unstable angina are decreased. It is now clear that most plaques that cause acute coronary syndromes (e.g., myocardial infarction and unstable angina) are angiographically shown to have <70% stenosis (reviewed in 28, 29). Approximately 60% of these lesions are caused by rupture of plaques with a large thrombogenic core of lipid and necrotic debris (including foci of macrophages, T cells, old hemorrhage, angiogenesis, and calcium). The ruptured cap is thin, presumably because macrophages secrete matrix metalloproteinases that digest it as they move across plaque, and because smooth muscle cells (the supporting element of the plaque) are depleted due to senescence or apoptosis caused by several factors, such as inflammatory cytokines.

WO 06/93932 discloses methods for the detection or diagnosis of atherosclerosis by measuring the level of eotaxin in an individual's serum. The application further suggests that detection of elevated eotaxin levels in serum may provide a means to diagnose atherosclerosis prior to the onset of symptoms.

None of the above publications teach or suggest eotaxin-2 as a target for therapeutic intervention for the treatment of inflammatory, autoimmune or cardiovascular diseases.

SUMMARY OF THE INVENTION

The present invention is based on the finding that inhibition of eotaxin-2 by polyclonal or monoclonal antibodies, has a significant protective effect in animal models of inflammatory diseases such as rheumatoid arthritis, experimental autoimmune encephalomyelitis (EAE), colitis, diabetes, and atherosclerosis. Without wishing to be bound by theory, the protective effects could be mediated, at least in part, by attenuation of the adhesive and migratory properties of the active inflammatory cells (lymphocytes and mononuclear cells). The present invention thus introduces eotaxin-2 as a novel target for developing therapeutics to treat inflammatory and/or autoimmune disorders. The invention also provides specific anti-eotaxin 2 antibodies for use alone or in combination with other therapeutic agents in the treatment of such disorders.

Inflammatory and/or autoimmune diseases include, for example, psoriasis, inflammatory bowel disease (IBD) (including ulcerative colitis and Crohn's disease), rheumatoid arthritis, diabetes, multiple sclerosis, systemic lupus erythematosus (SLE), scleroderma and pemphigus.

Accordingly, by a first of its aspects, the present invention provides a pharmaceutical composition for treating inflammatory, autoimmune or cardiovascular diseases comprising at least one eotaxin-2 antagonist and a pharmaceutically acceptable carrier or excipient.

In one embodiment said eotaxin-2 antagonist is an anti eotaxin-2 antibody or a fragment thereof which retains the binding activity of the antibody.

The anti-eotaxin-2 antibody may be a monoclonal antibody or a polyclonal antibody. In certain embodiments the anti-eotaxin-2 antibodies are human antibodies, humanized antibodies or chimeric antibodies.

In certain specific embodiments, said anti-eotaxin-2 antibody is a monoclonal antibody secreted by hybridoma D8 (ECACC Accession No. D809081702), hybridoma G7, or hybridoma G8 (ECACC Accession No. G80908170) or a fragment thereof which retains the binding activity of the antibody.

In certain specific embodiments, said anti-eotaxin-2 antibody is a monoclonal antibody selected from the group consisting of:
  a. a monoclonal antibody comprising a heavy chain encoded by a nucleic acid having at least 90% homology with SEQ ID NO: 1 and a light chain encoded by a nucleic acid having at least 90% homology with SEQ ID NO: 2;
  b. a monoclonal antibody comprising a heavy chain encoded by a nucleic acid having at least 90% homology with SEQ ID NO: 3 and a light chain encoded by a nucleic acid having at least 90% homology with SEQ ID NO: 4;
  c. a monoclonal antibody comprising a heavy chain encoded by a nucleic acid having at least 90% homology with SEQ ID NO: 5 and a light chain encoded by a nucleic acid having at least 90% homology with SEQ ID NO: 6,
  d. a monoclonal antibody comprising a heavy chain encoded by a nucleic acid having at least 90% homology with the nucleic acid encoding the heavy chain of the monoclonal antibody secreted by hybridoma D8 (ECACC Accession No. D809081702), hybridoma G7, or hybridoma G8 (ECACC Accession No. G80908170) and a light chain encoded by a nucleic acid having at least 90% homology with the nucleic acid encoding the light chain of the monoclonal antibody secreted by hybridoma D8 (ECACC Accession No. D809081702), hybridoma G7, or hybridoma G8 (ECACC Accession No. G80908170); and
  e. any fragment of the antibodies of a-d which retains the binding activity of the antibody.

In another embodiment, the eotaxin-2 antagonist is an antisense molecule or a siRNA molecule directed against eotaxin-2 mRNA.

In another embodiment, the eotaxin-2 antagonist is a small molecule chemical.

In certain embodiments said inflammatory, autoimmune or cardiovascular disease is selected from the group consisting of atherosclerosis, rheumatoid arthritis, inflammatory bowel disease, multiple sclerosis and diabetes.

By another aspect, the present invention provides a method of treating inflammatory or autoimmune diseases comprising administering to a patient in need thereof a therapeutically effective dose of an eotaxin-2 antagonist or the pharmaceutical composition of the invention.

In accordance with certain embodiments of the invention, said autoimmune disease is selected from the group consisting of rheumatoid arthritis, inflammatory bowel disease (e.g. colitis), multiple sclerosis and diabetes.

By yet another aspect, the present invention provides a method of inhibiting atherosclerotic plaque formation comprising administering to a patient in need thereof a therapeutically effective dose of an eotaxin-2 antagonist or the pharmaceutical composition of the invention.

The invention also provides a method for stabilizing an atherosclerotic plaque comprising administering to a patient in need thereof a therapeutically effective dose of an eotaxin-2 antagonist or the pharmaceutical composition of the invention.

The invention also provides a method for preventing major cardiovascular events in a patient with acute coronary syndrome comprising administering to said patient a therapeutically effective dose of an eotaxin-2 antagonist or the pharmaceutical composition of the invention.

The methods of the invention also encompass administration of said eotaxin-2 antagonist or said pharmaceutical composition in combination with at least one additional therapeutic agent.

In accordance with certain embodiments said at least one additional therapeutic agent is selected from a group consisting of chemotherapeutics, cytokines, peptides, antibodies and antibiotics.

For the treatment of rheumatoid arthritis, said additional therapeutic agent includes, but is not limited to methotrexate, a steroid, anti-TNFα antibodies, anti TNF receptor antibodies, anti-IL6 receptor antibodies, or anti-CD20 antibodies.

For the treatment of IBD (inflammatory bowel disease), said additional therapeutic agent includes, but is not limited to, cyclosporine, NSAIDS (non-steroidal anti inflammatory drugs), steroids, or anti TNF antibodies (e.g. Infliximab).

For the treatment of multiple sclerosis, said additional therapeutic agent includes, but is not limited to, copaxone, interferon-beta, intravenous immune globulin (IVIG), or a monoclonal antibody to VLA-4 (e.g. Tysabri).

In accordance with one embodiment of the invention said at least one additional therapeutic agent is administered simultaneously with the eotaxin-2 antagonist or said pharmaceutical composition.

In accordance with another embodiment of the invention said at least one additional therapeutic agent and said eotaxin-2 antagonist or said pharmaceutical composition are administered sequentially.

In another aspect, the present invention provides a hybridoma cell line secreting an anti-eotaxin 2 monoclonal antibody, wherein said hybridoma is selected from the group consisting of D8 (ECACC Accession No. D 809081702), G7, or G8 (ECACC Accession No. G809081701).

The present invention also provides a monoclonal antibody directed against eotaxin-2, or any fragment thereof which retains the binding ability to eotaxin 2, wherein said monoclonal antibody is secreted from hybridoma D8 (ECACC Accession No. D 809081702), G7, or G8 (ECACC Accession No. G809081701).

In certain embodiments, the present invention provides a monoclonal antibody directed against eotaxin-2 wherein said antibody is a monoclonal antibody selected from the group consisting of:
  a. a monoclonal antibody comprising a heavy chain encoded by a nucleic acid having at least 90% homology with SEQ ID NO: 1 and a light chain encoded by a nucleic acid having at least 90% homology with SEQ ID NO: 2;
  b. a monoclonal antibody comprising a heavy chain encoded by a nucleic acid having at least 90% homology with SEQ ID NO: 3 and a light chain encoded by a nucleic acid having at least 90% homology with SEQ ID NO: 4;
  c. a monoclonal antibody comprising a heavy chain encoded by a nucleic acid having at least 90% homology with SEQ ID NO: 5 and a light chain encoded by a nucleic acid having at least 90% homology with SEQ ID NO: 6,
  d. a monoclonal antibody comprising a heavy chain encoded by a nucleic acid having at least 90% homology with the nucleic acid encoding the heavy chain of the antibody secreted from hybridoma D8 (ECACC Accession No. D 809081702), G7, or G8 (ECACC Accession No. G809081701) and a light chain encoded by a nucleic acid having at least 90% homology with the nucleic acid encoding the light chain of the antibody secreted from hybridoma D8 (ECACC Accession No. D 809081702), G7, or G8 (ECACC Accession No. G809081701); and
  e. any fragment of the antibodies of a-d which retains the binding activity of the antibody.

The invention further relates to an isolated nucleic acid molecule encoding the monoclonal antibody of the invention, or antigen-binding portion thereof, as well as to an expression vector comprising the nucleic acid molecule and a host cell comprising the expression vector.

In certain embodiments, the expression vector is capable of replicating in prokaryotic or eukaryotic cell lines.

In another aspect, the present invention also provides use of eotaxin-2 antagonists in the treatment of inflammatory and autoimmune diseases. In one embodiment said eotaxin-2 antagonists are antibodies.

The invention also encompasses use of eotaxin-2 antagonists in the preparation of pharmaceutical compositions for treatment of inflammatory and autoimmune diseases. In one embodiment said eotaxin-2 antagonists are antibodies.

BRIEF DESCRIPTION OF THE DRAWINGS

In order to understand the invention and to see how it may be carried out in practice, embodiments will now be described, by way of non-limiting example only, with reference to the accompanying drawings, in which.

Control animals were treated with PBS or IgG. [I] represents the extent (size) of the lesions; [II] represents the inflammation (inflammatory cell infiltration); and [III] represents the damage (tissue destruction).

Figure 10:
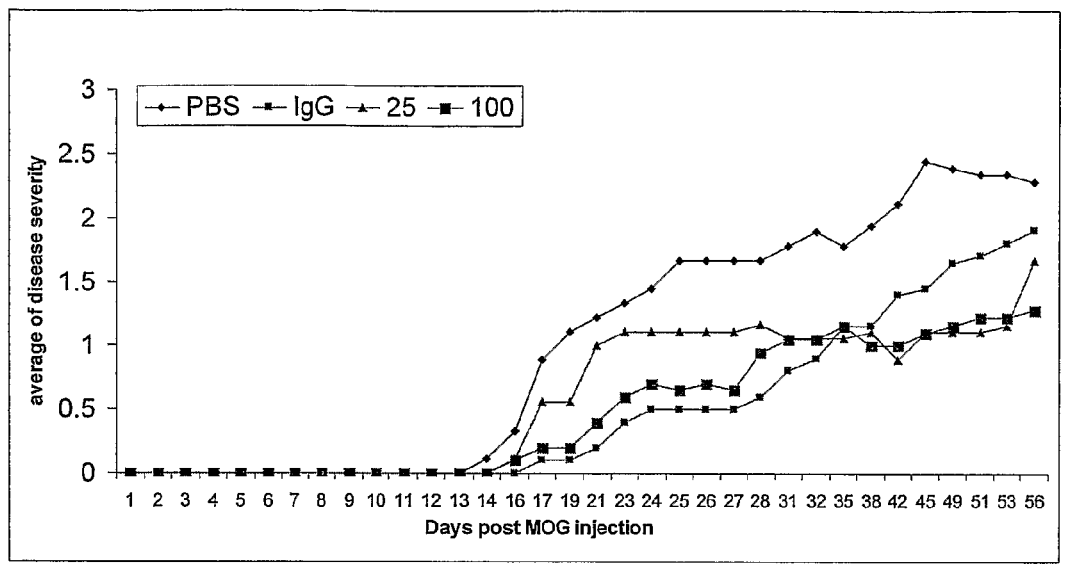

FIG. 10 is a graph showing the average of disease severity as a function of time in mice with induced EAE, treated with either PBS, IgG, anti-eotaxin-2 antibody D8 (25 μg) or anti-eotaxin-2 antibody D8 (100 μg).

Figure 11A:
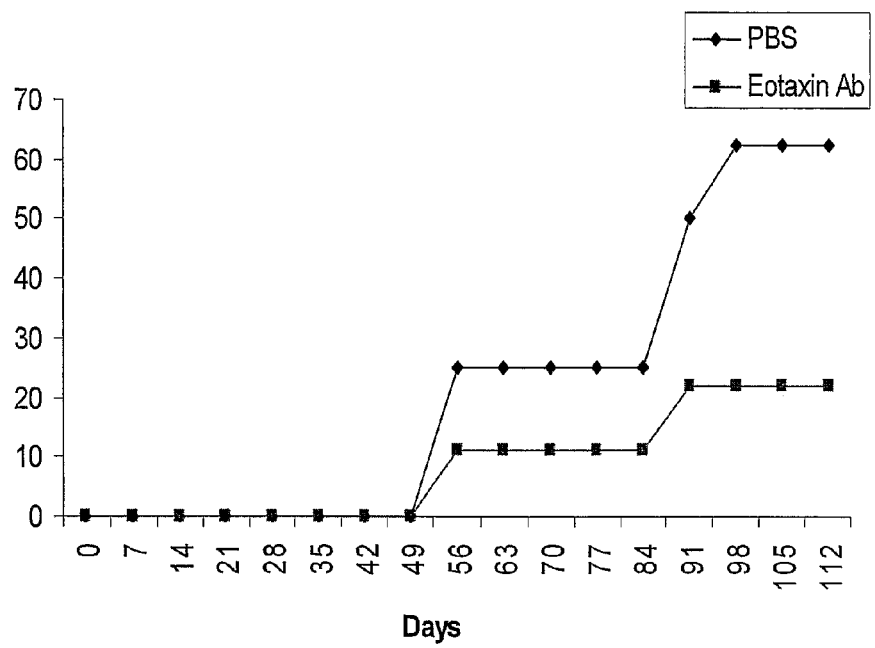

FIG. 11A is a graph showing the disease incidence (percent of diabetic mice) as a function of time in NOD mice, treated with either PBS, or an anti-eotaxin-2 antibody (D8).

Figure 11B:
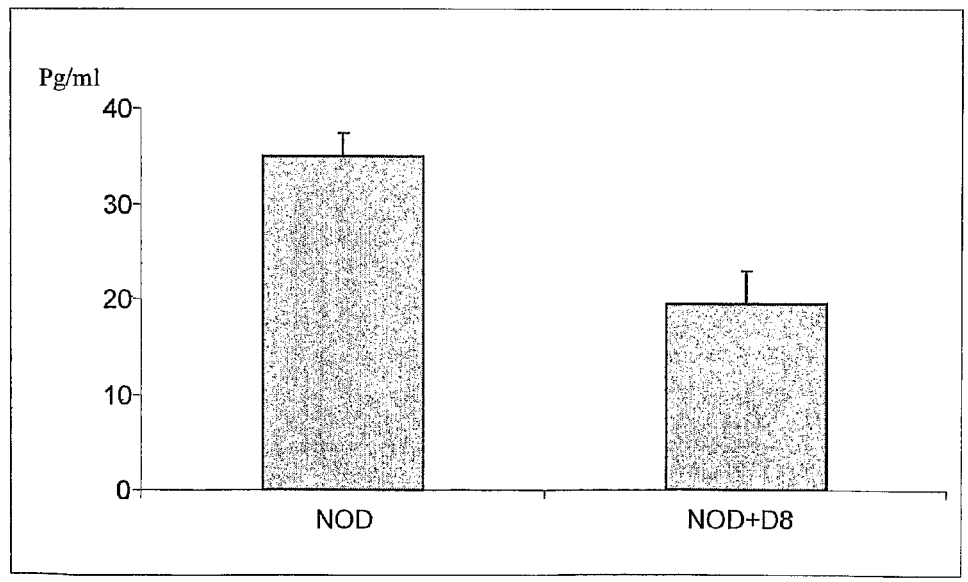

FIG. 11B is a graph showing eotaxin-2 levels (pg/ml) in the serum of NOD mice, treated with either PBS, or an anti-eotaxin-2 antibody (D8).

Figure 12A:
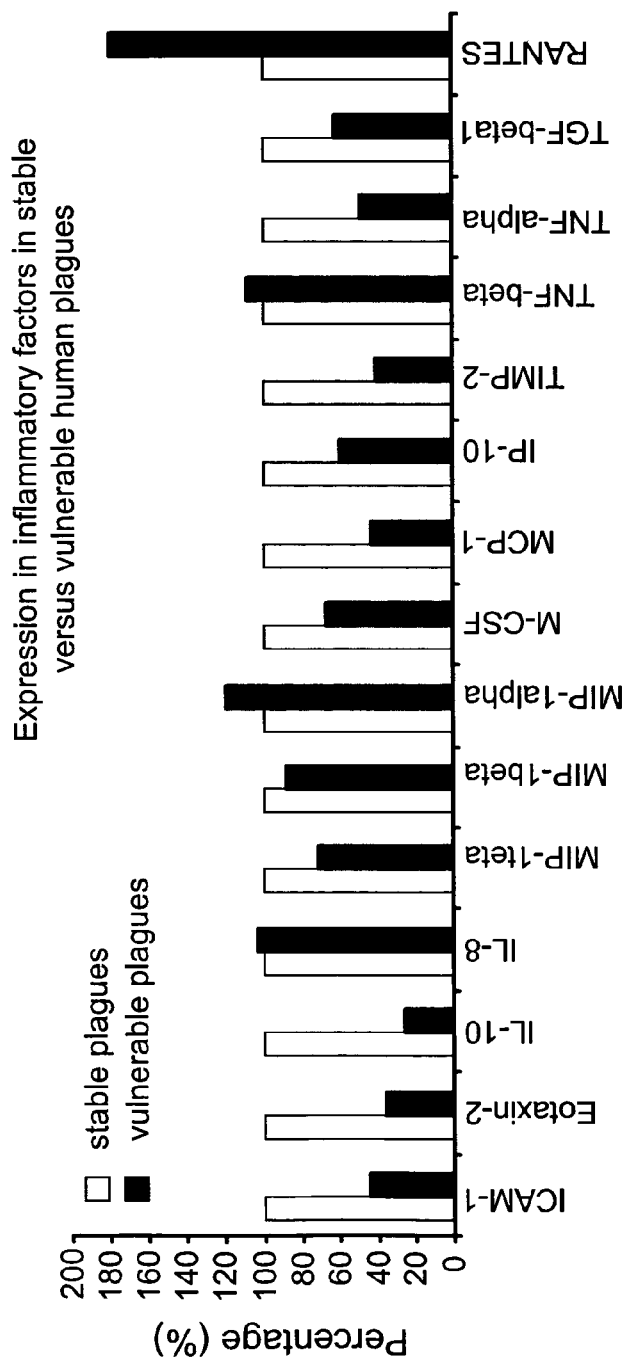

FIG. 12A is a graph showing the quantitative analysis of expression of inflammatory factors in stable versus vulnerable plaques. 4 plaques were analyzed in each group.

Figure 12B:
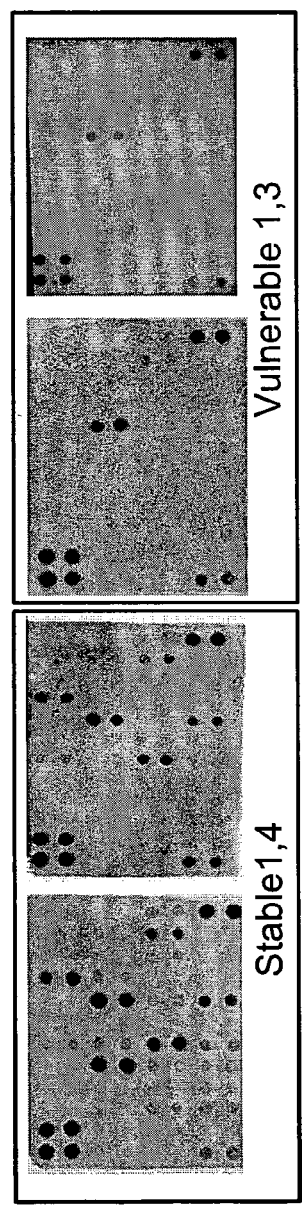
Figure 13A:
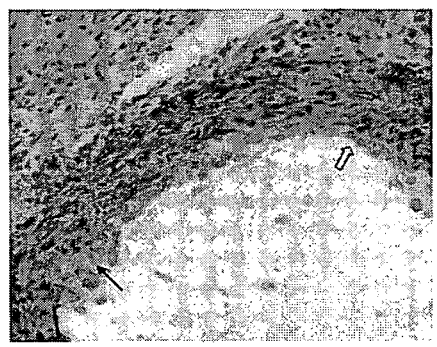
Figure 13B:
Figure 13C:
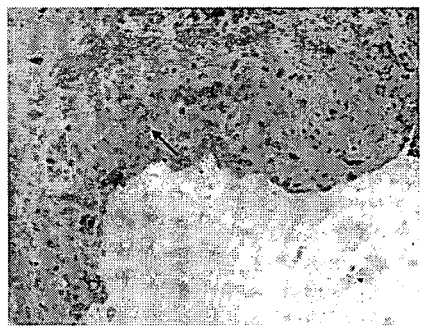
Figure 13D:
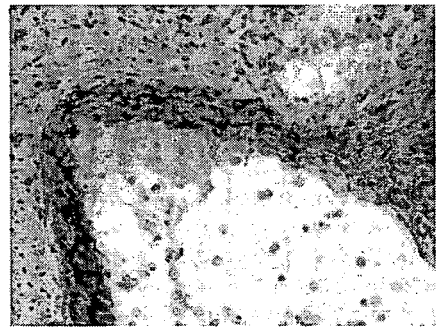

FIG. 12B is an image providing representative examples.

FIG. 13 is an image demonstrating Immunohistochemical localization of eotaxin-2 in murine atheroma. FIG. 13A shows a characteristic fatty streak (AHA class I-II), FIG. 13B shows an intermediate plaque (AHA class II), FIG. 13C shows an atheromatous lesion (AHA class III-IV) and FIG. 13D shows a negative control stained with an irrelevant IgG. Thick arrow shows representative endothelial cells positive for eotaxin-2 whereas thin arrow shows the respective staining within plaque macrophages.

Figure 14A:
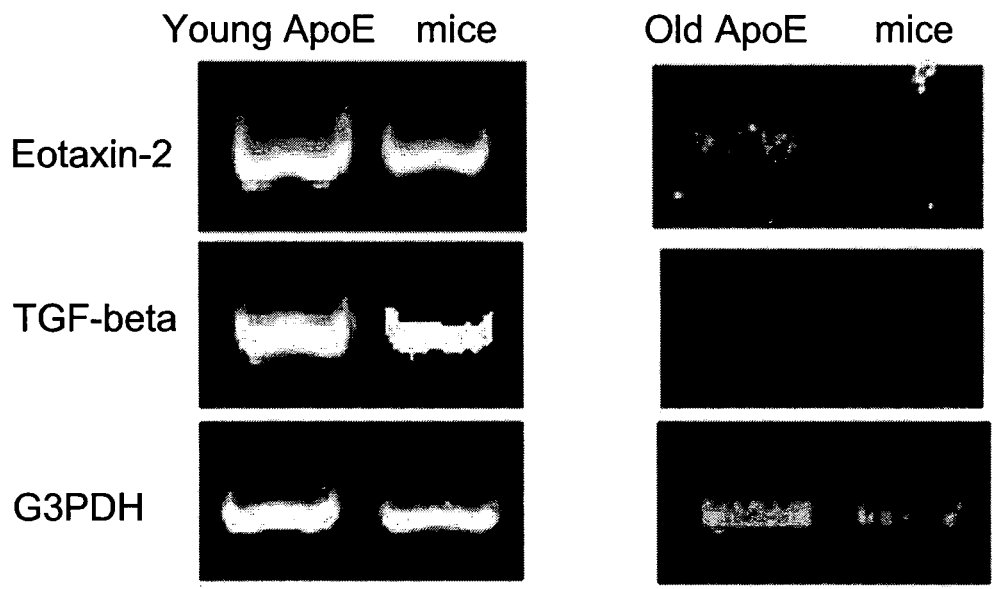
Figure 14B:
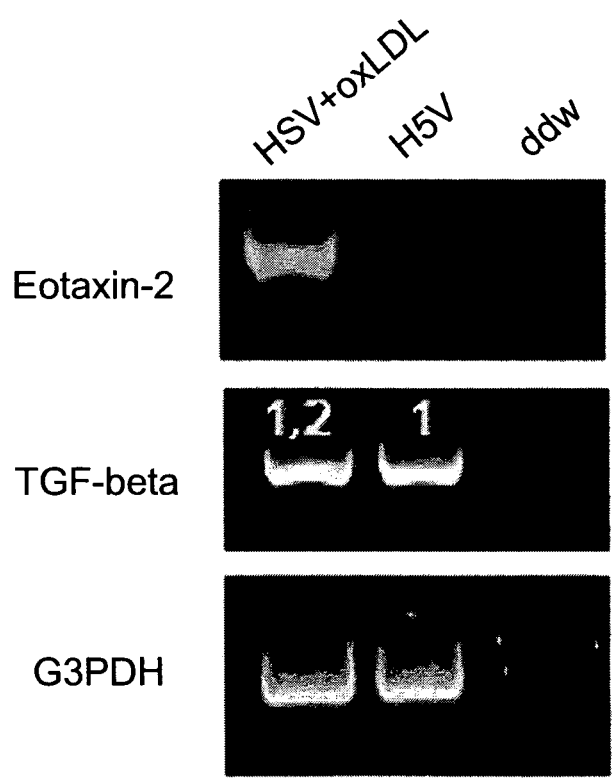

FIG. 14A is an image of a gel demonstrating eotaxin-2 and TGFβ mRNA expression in aortas of young and old KO ApoE mice. FIG. 14B is an image of a gel showing the expression of eotaxin-2 and TGF-beta mRNA in murine H5V endothelial cells incubated with oxLDL.

Figure 15A:
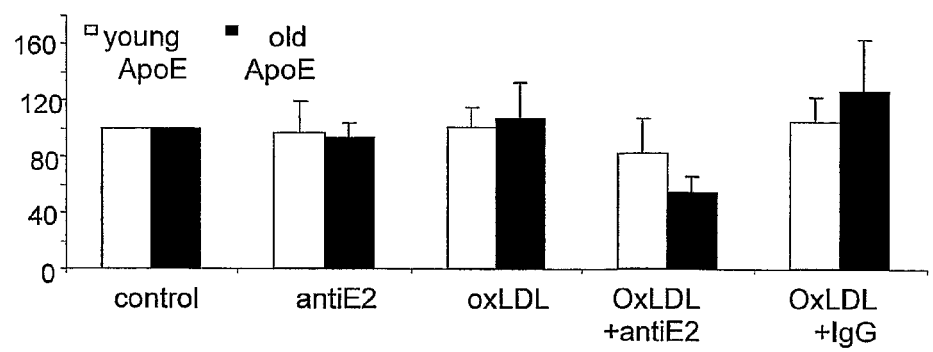
Figure 15B:
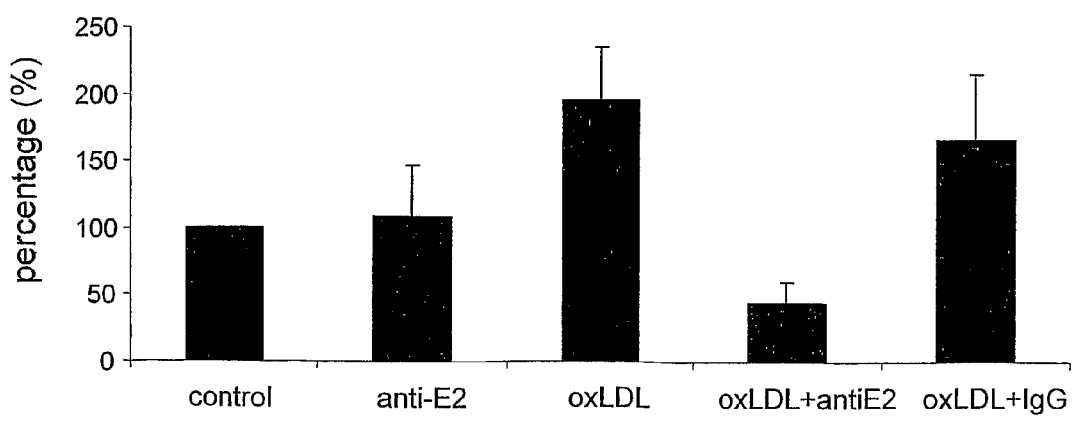
Figure 16A:
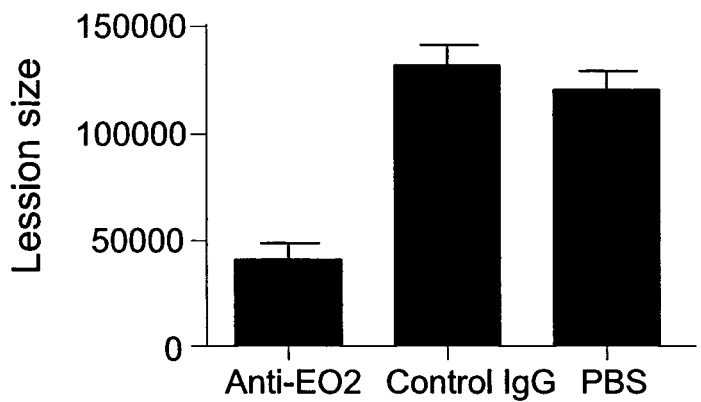
Figure 16B:
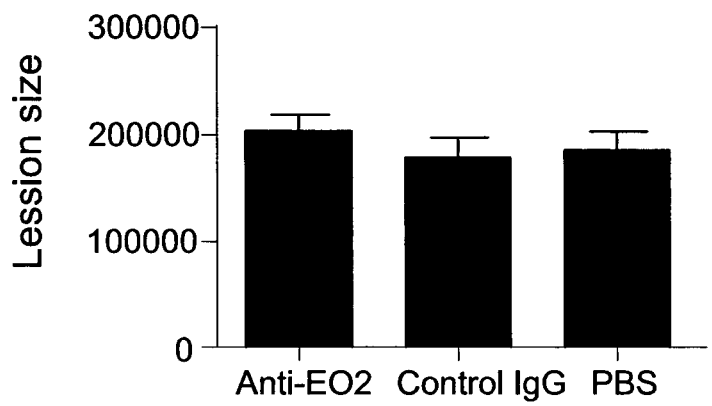
Figure 16C:
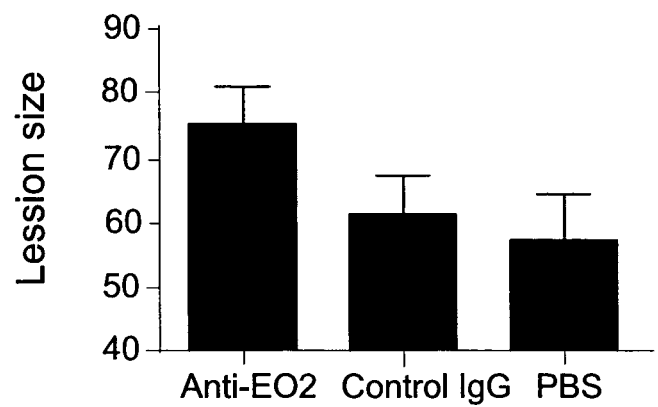

FIG. 15A is a graph showing the effect of eotaxin-2 blockade on adhesion of mononuclear cells (splenocytes) onto endothelium. FIG. 15B shows representative results performed with monocyte-macrophage cell line in an essentially similar protocol. $*p<0.05$ FIG. 16A is a graph showing lesion (plaque) size in response to treatment with anti eotaxin-2 antibodies for 4 weeks. FIG. 16B is a graph showing lesion size in response to treatment with anti eotaxin-2 antibodies for 10 weeks. FIG. 16C is a graph showing % fibrous area in response to treatment with anti eotaxin-2 antibodies for 10 weeks $*p<0.01$; $**p<0.05$.

FIG. 17 is an image of representative sections from apoE mice treated with blocking antibodies to eotaxin-2. FIG. A-C show representative oil-red O stained fatty streak lesions from PBS, control IgG an eotaxin2 ab treatment, respectively. FIG. 17D-F show similar assessment of the more advanced lesions in the longer treatment studies with similar groups of mice. FIGS. 17 G-I and J-L show Masson's trichrom and von Giesson's histochemistry (respectively) studies from either PBS, control IgG-2 antibodies treatments, respectively.

DETAILED DESCRIPTION OF THE INVENTION

The present invention relates to antibodies which bind specifically to eotaxin 2 (CCL24) and inhibit its function. Furthermore, the invention relates to pharmaceutical compositions comprising the antibodies, and to their use for the treatment of inflammation, autoimmune and cardiovascular diseases.

In order for the present invention to be more readily understood, various definitions are set forth throughout the detailed description.

According to one aspect, the method of treatment of the invention is effected by providing to a patient in need thereof a therapeutically effective amount of an eotaxin-2 antagonist capable of reducing activity and/or expression of eotaxin 2, thereby reducing the inflammatory, autoimmune or atherosclerosis disease in the patient.

As used herein the term "patient" refers to a subject that may benefit from the present invention such as a mammal (e.g. canine, feline, ovine, porcine, equine, bovine, or human). In one specific embodiment the patient is human.

As used herein the term "treatment" refers to reducing, preventing, curing, reversing, attenuating, alleviating, minimizing suppressing or halting the deleterious effects of a disease or a condition that is mediated by eotaxin 2.

The terms "eotaxin 2" (eosinophil chemotactic protein 2), "CCL24" (Chemokine (C—C motif) ligand 24) or "MPIF-2" (myeloid progenitor inhibitory factor 2) are used interchangeably and refer to a cytokine belonging to the CC chemokine family which is encoded by the human CCL24 gene, located on human chromosome 7, and which is known in the art.

CCL24 interacts with chemokine receptor CCR3. CCL24 activity refers to induction of chemotaxis in eosinophils, basophils, T lymphocytes and neutrophils, as well as induction of angiogenic and migratory responses in endothelial and smooth muscle cells.

As used herein the term "inflammation" refers to the complex biological response of the immune system to harmful stimuli, such as pathogens, damaged cells (caused by e.g. burns, trauma, neoplasma) or irritants such as chemicals, heat or cold. The term "inflammatory disease" refers to diseases associated with inflammation, including, but not limited to atherosclerosis and various autoimmune diseases.

As used herein the term "atherosclerosis" (also known as Arteriosclerotic Vascular Disease or ASVD) is a pathological condition in which an artery wall thickens as the result of a build-up of fatty materials such as cholesterol. This process is a result of a chronic inflammatory response in the walls of arteries, in large part due to the accumulation of macrophages and promoted by low-density lipoproteins without adequate removal of fats and cholesterol from the macrophages by functional high density lipoproteins (HDL). This hardening or furring of the arteries is caused by the formation of multiple plaques within the arteries.

An Atherosclerotic plaque or arethoma is an accumulation and swelling in artery walls that is made up of cells (mostly macrophage cells), or cell debris, that contain lipids (cholesterol and fatty acids), calcium and a variable amount of fibrous connective tissue. Atheroma and changes in the artery wall usually result in small aneurysms (enlargements) just large enough to compensate for the extra wall thickness with no change in the lumen diameter. The mature plaque is composed of two basic structures: the lipid core and the fibrous cap. The smaller the lipid core and the thicker the fibrous cap, the more stable the plaque is, meaning that its propensity to rupture and cause myocardial infarction or unstable angina are decreased. It is now clear that most plaques that cause acute coronary syndromes (e.g., myocardial infarction and unstable angina) are angiographically shown to have <70% stenosis (reviewed in 28, 29). Approximately 60% of these lesions are caused by rupture of plaques with a large thrombogenic core of lipid and necrotic debris (including foci of macrophages, T cells, old hemorrhage, angiogenesis, and calcium).

As used herein the term "cardiovascular disease" (CVD) refers to disorders that can affect the heart (cardio) and/or the body's system of blood vessels (vascular). Most cardiovascular diseases reflect chronic conditions—conditions that develop or persist over a long period of time. However, some of the outcomes of cardiovascular disease may be acute events such as heart attacks and strokes that occur suddenly when a vessel supplying blood to the heart or brain becomes blocked. CVD also encompasses diseases that are associated with atherosclerosis, coronary heart disease (CHD) and coronary artery disease (CAD)—disease of the blood vessels supplying the heart that may lead to Angina (including unstable angina and new onset angina)—intense chest pain or even heart attack—myocardial infarction, and ST- or NON-ST elevation.

As used herein the term Autoimmune disease describes a pathological condition resulting from an overactive immune response of the body against substances and tissues normally present in the body. The immune system mistakes some part of the body as a pathogen and attacks it. This may be restricted to certain organs or involve a particular tissue in different places which may affect the basement membrane in both the lung and the kidney. Examples of autoimmune diseases including at least all the exemplified diseases such as rheumatoid arthritis, multiple sclerosis and colitis, as well as prominent examples which include amongst others, coeliac disease, Diabetes Melitus type I (IDDM), systemic lupus erythematosus (SLE), Sjorgen's syndrome, Churg-Strauss Syndrome, Hashimoto's thyroditis, Graves' disease, psoriasis, inflammatory bowel disease (ulcerative colitis and Crohn's disease), scleroderma and pemphigus.

As used herein the term "eotaxin 2 antagonist" refers to a molecule that interacts with eotaxin 2/CCL24 and blocks or depresses the normal activity or expression of the cytokine. A number of agents can be used in accordance with this aspect of the invention. Thus, for example the antagonist can be an antibody which inhibits the activity of eotaxin 2, a small molecule chemical, siRNA, DNAzye, ribozyme, or an antisense polynucleotide.

In the context of the present invention the term "anti eotaxin-2 antibody" encompasses polyclonal antibodies and monoclonal antibodies. Furthermore, the antibodies may be for example murine antibodies, chimeric antibodies, humanized antibodies and human antibodies. The term refers to whole antibody molecules as well as functional fragments thereof that are capable of binding to eotaxin 2, such as single chain (SC) antibodies, Fab, F(ab')$_2$ or Fv antibody fragments, as well as any combination thereof.

Methods for the purification of serum immunoglobulins ("polyclonal antibodies") or reactive portions thereof are well known in the art including precipitation by ammonium sulfate or sodium sulfate followed by dialysis, ion exchange chromatography, affinity chromatography, and gel filtration.

As used herein the term "Monoclonal antibodies" (also termed mAb or moAb) refers to identical, monospecific antibodies that are produced by a single clone of cells. Methods of generating and isolating monoclonal antibodies are well known in the art, e.g. as shown in the Examples section which follows. The present invention also encompasses chimeric or humanized antibodies. As used herein the term humanized antibodies refers to antibodies or fragments thereof having a human backbone and carrying non-human-derived complementarity determining regions (CDRs). The non-human CDRs can be obtained for example from mouse, rat, rabbit or goat antibodies having a desired specificity, affinity and/or capacity. In certain embodiments, additional amino acids are replaced in the human antibody framework with their non-human counterparts to improve the antibody's binding properties. As used herein "chimeric antibodies" are antibodies or fragments thereof that contain polypeptides originating from different species, for example, a mouse-human antibody chimera obtained by substituting the mouse Fc region of the antibody with that of a human.

Methods for making humanized antibodies are well known in the art. Humanized antibodies can be prepared by inserting the appropriate CDR coding segments (responsible for the desired binding properties) into a human antibody "framework". This is achieved through recombinant DNA methods using an appropriate vector and expression in host cells (e.g. mammalian cells). That is, after a monoclonal antibody having the desired properties is developed in a mouse (or other non-human animal), the DNA coding for that antibody is isolated, cloned into a vector and sequenced. The DNA sequence corresponding to the antibody CDRs can then be determined. Once the precise sequence of the desired CDRs is known, a strategy can be devised for inserting these sequences appropriately into a construct containing the DNA for a human antibody variant.

The present invention further encompasses fragments of anti eotaxin 2 antibodies which retain the binding activity to eotaxin 2.

As used herein the term "Fab" refers to a fragment which contains a single, monovalent antigen-binding fragment of an antibody molecule. A Fab includes one intact light chain and a portion of a heavy chain and can be produced by digestion of the whole antibody with papain.

As used herein the term "(Fab)$_2$" refers to an antibody fragment obtained by pepsin digestion of a whole antibody. Pepsin digestion results in cleavage of the antibody at the Fc portion, resulting in a divalent fragment which contains two Fab fragments and a small portion of the Fc fragment and which are joined by S—S bonds. "Fab'" is obtained by reduction of (Fab)$_2$ resulting in opening of the S—S bonds.

As used herein the term "Fv" refers to a genetically engineered fragment containing the variable region of the light chain and the variable region of the heavy chain.

As used herein the term "single chain antibody" refers to a genetically engineered molecule containing the variable region of the light chain and the variable region of the heavy chain, linked by a suitable linker (e.g. a polypeptide). Single chain antibodies are typically prepared by expressing a single polynucleotide encoding a fusion polypeptide including the light and heavy chain variable regions and the linker. Methods for preparing single chain antibodies are well known in the art, for example see U.S. Pat. No. 4,946,778.

Antibody fragments in accordance with the present invention can be prepared by proteolytic hydrolysis of the antibody using suitable proteases e.g. papain or pepsin, or by recombinant expression of a nucleic acid encoding the antibody fragments in host cells such as bacteria (e.g. *E. Coli*) or mammalian cells (e.g. Chinese Hamster Ovary (CHO) cells).

Antibodies of the invention may be recombinantly produced by expressing nucleic acids encoding the antibodies in suitable host cells using expression vectors. As used herein, the term "expression vector" refer to a nucleic acid construct capable of transferring the genetic information encoding the anti eotaxin 2 antibody chains to cells. The insert is expressed in the target cell, antibodies are produced and either secreted to the cell's media or extracted directly from the cells. Vectors can be of various origins for example, but not limited to, plasmids, bacteriophages and other viruses, cosmids, and artificial chromosomes. Typically, engineered vectors comprise an origin of replication, a cloning site, a selectable marker and a heterologous nucleic acid encoding the antibody of the invention. Viral vectors are generally genetically-engineered viruses carrying modified viral DNA or RNA that has been rendered noninfectious, but still contain viral promoters and the heterologous nucleic acid, thus allowing for translation of the heterologous nucleic acid using a viral promoter. Non-limiting examples of viral vectors are: recombinant retroviruses (including lentiviruses), adenoviruses, adeno-associated viruses, SV40, Herpes Simplex and vaccinia virus.

In certain embodiments, the present invention also encompasses immunoconjugates and bispecific molecules comprising the antibodies of the invention.

As used herein the term "Antisense therapy" refers to a form of treatment which involves inhibition of the expression of a gene known to affect a particular disease. In the context of the present invention antisense therapy is aimed at the inhibition of expression of eotaxin 2 mRNA. Hence, antisense therapy involves the synthesis of a strand of nucleic acid (DNA, RNA or a chemical analogue) which is complementary to the sequence of eotaxin 2 mRNA or a fragment thereof (the antisense oligonucleotide) that will bind to the messenger RNA (mRNA) produced by that gene and inactivate it, effectively turning that gene "off".

As used herein the term "siRNA" (Small interfering RNA), also known as short interfering RNA or silencing RNA, is a class of double stranded RNA molecules, typically 20-25 nucleotides in length, that play a variety of roles in biology. Most notably, siRNA is involved in the RNA interference (RNAi) pathway, where it interferes with the expression of a specific gene.

As used herein the term "small molecule chemical" refers to an organic compound. The upper molecular weight limit for a small molecule is approximately 800 Daltons.

As used herein the term "Methotrexate", refers to an antimetabolite and antifolate drug used in treatment of cancer and autoimmune diseases.

Pharmaceutical compositions comprising antibodies of the present invention are useful for parenteral administration, i.e., subcutaneously, intramuscularly and intravenously. The compositions for parenteral administration commonly comprise the antibody dissolved in an acceptable carrier or excipient, preferably an aqueous carrier. A variety of aqueous carriers can be used, e.g., water, buffered water, saline, PBS (phosphate buffered saline) and the like. These solutions are sterile and generally free of particulate matter. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, histidine and arginine.

Methods for preparing compositions for parenteral administration are known or apparent to those skilled in the art and are described in more detail in, for example, Remington's Pharmaceutical Science (15th Ed., Mack Publishing Company, Easton, Pa., 1980).

The antibodies of the invention can be frozen or lyophilized for storage and reconstituted in a suitable carrier prior to use. This technique has been shown to be effective with conventional immunoglobulins and art-known lyophilization and reconstitution techniques can be employed.

For therapeutic purposes, compositions are administered in an amount sufficient to treat or at least partially alleviate the condition and its complications. An amount adequate to accomplish this is defined as a "therapeutically effective dose". Amounts effective for this use depend upon the severity of the condition and the general state of the patient's own immune system, but generally range from about 0.01 to about 150 mg of antibody per dose. Single or multiple administrations on a daily, weekly or monthly schedule can be carried out with dose levels and pattern being selected by the treating physician.

EXAMPLES

Production of Monoclonal Antibodies

Several clones of mAbs were produced according to standard protocols. In short, Balb/C mice were immunized with 20 µg of eotaxin-2 (Peprotec, USA) followed by four additional boosts. After confirming the presence of polyclonal anti-eotaxin-2 Abs in the sera, mice were sacrificed, cells were isolated from their spleens and hybridized with an NS/0 myeloma line, followed by clonal screening for binding to eotaxin-2. The hybridomas were then grown in serum-free media for 2-3 weeks, media collected and concentrated by 100 kDa centricons (Biological Industries, Israel). Cross-reactivity of one of the mAbs (D8) with murine eotaxin-2 was confirmed by ELISA.

The following primers were used for determining the nucleic acid sequence of the monoclonal antibodies D8, G8, and G7:

Heavy Chain (IgG Gamma-1):

```
Forward (SEQ ID NO: 7):
5' CGAAGAGACAGTGACCAGAGTCCCTTGGCCCCAGTAAGCAAAGCTA
TTACCGAAGGTACAGTAATACACGGCCGTGTC 3'

Reverse (SEQ ID NO: 8):
5' CGGGGAAGTAGTCCTTGACCAGGC 3'
```

Light Chain (Kappa):

```
    Forward (SEQ ID NO: 9):
    (Degenerate) 5' RR HRYY BWDMTVACHARWC 3'
    Or (SEQ ID NO: 10):
    5' GATGTCTTGTGAGTGGCCTCAC 3'

Reverse (SEQ ID NO: 11):
    5' TGGGATAGAAGTTATTCAGCAGGC 3'
```

Binding Assays

Plates were coated with 1 µ/ml of either eotaxin or eotaxin-2 (in buffer Carbonate), overnight at 4° C. The plates were washed with PBS 3 times and blocked with 2% BSA for 45 minutes at 37° C. Anti eotaxin-2 antibodies (the D8 clone) was put in serial dilutions in PBS for 1.5 hour at 37° C. Washing was repeated as indicated above and the plates were incubated for 1 hour at 37° C. with a goat anti-mouse peroxidase conjugated antibody. Washing was repeated as above and binding was detected using a colorimetric substrate.

Splenocyte Adhesion Assays

In adhesion assays, C57Bl mice and Lewis rat splenocytes were separated on ficoll gradient and plated in 10 cm dishes for an overnight incubation. On the next day cells were harvested and pretreated with increasing concentrations of D8 or total mouse IgG (5-50 ug/ml) for two hours with rotation. Cells were then centrifuged and plated on 96-well plates pre-coated with fibronectin. After one hour-incubation, non-adherent cells were washed away and the amount of adherent cells was analyzed using XTT kit (Biological Industries, Israel). Similar adhesion assays were performed using peripheral blood mononuclear cells (PBMCs) collected from healthy donors.

Migration Assays

C57BL/6J-derived splenocytes, as well as rat splenocytes and human PBMCs pretreated with D8 (30 ug/ml) were plated onto the upper chamber of a Trans-Well system. The lower chamber contained serum-free media supplemented with VEGF (vascular endothelial growth factor) (20 ng/ml).

Four hours later the media in the lower chamber was collected and cells counted using flow cytometry (number of cells collected per minute).

Plaques and Cardiovascular In Vitro Studies:

I. Human Carotid Plaque Preparation and Protein Array

Human atherosclerotic plaques were recovered from two groups of patients. Stable plaques (n-4) were obtained from endarterectomy specimens of patients with asymptomatic severe carotid atherosclerosis. Representative of unstable plaques were specimens obtained upon percutaneous coronary angioplasty of culprit vessels from patients with acute myocardial infarctions (n=4). Thrombectomies were performed by dedicated suction devices. The obtained material consists of red thrombi, white thrombi and fragments of vulnerable plaques from the culprit artery. After washing and lysis, the remaining tissue comprises predominantly fragments of atherosclerotic ruptured plaques.

The RayBio™ Human Inflammation Antibody Array 3.1 (Ray Biotech, USA) was used for detection of 40 cytokines, chemokines and growth factors in stable and vulnerable human plaques. Briefly, plaques were homogenized in lysis buffer provided within the kit using pellet pestle. Arrays were incubated with 500 mg of protein of each sample and developed following the manufacturer's instructions. The results were analyzed using TINA 2.0 program.

II. Capillary Cells

Murine capillary cells (H5V) were cultured in DMEM F-12 (Biological Industries, Israel) supplemented with 10% fetal calf serum (FCS) (Invitrogen) and 1% penicillin/streptomycin sulfate (Biological Industries, Israel). The cells were maintained at 37° C. in a humid incubator with 8% $CO_2$. Monocytoid U937 cells were cultured in complete medium RPMI 1640, containing 10% FCS and 1% penicillin/streptomycin sulfate at a concentration of $10^6$ cells/ml. The cells were maintained at 37° C. in 5% $CO_2$ humid incubator.

III. Adhesion Assay with Endothelial Cells

In adhesion assays, H5V mouse endothelial cells were incubated for 72 h in presence of oxLDL, 1 µg/ml (prepared as previously described, 33). Then the cells were plated overnight in 96 well plates at concentration $4 \times 10^3$ cells/well in presence of oxLDL, 1 µg/ml. On the next day, the cells were pretreated with the neutralizing goat anti mouse eotaxin-2 antibody (Cytolab, USA) or goat IgG for one hour before U937 cells or spleen-derived lymphocytes from ApoE mice were added at a concentration of $8 \times 10^4$/well. After one hour-incubation, non-adherent cells were washed away and the amount of adherent cells was analyzed using XTT kit (Biological Industries, Israel).

IV. PCR Analysis of Aortas and H5V Endothelial Cells

RNA from tissue samples and H5V endothelial cells was isolated by the guanidinium thiocyanate and phenol chloroform method using EZ-RNA kit (Biological Industries, Israel) following the manufacturer's protocol. RT-PCR was carried out using AMV reverse transcriptase (TaKaRa RNA PCR kit, Takara, Japan) in a conventional thermocycler. Specific gene amplification was performed using hot start TaKaRa Ex Taq DNA polymerase. Specific primers that do span intronic sequences were designed for mouse mRNA of eotaxin-2 and TGF-beta (Table 1). The following PCR conditions were used for amplification of G3PDH and TGF-beta: incubation of the samples at 95° C. for 2 min and then 27 cycles (for G3PDH) or 35 cycles (for TGFbeta) consisting of 95° C. for 30 s; 55° C. for 45 s and 72° C. for 1 min. Touchdown PCR amplification protocol was used for analysis of eotaxin-2 mRNA expression: with the starting temperature 70° C. and amplification for 30 cycles at annealing temperature of 60° C. PCR samples were run on a 2% agarose gel stained with Gelstar Nucleic Acid Stain (Gambrex, USA), and the PCR products were visualized with 300 nm UV transilluminator and photographed with Polaroid camera system. The absence of genomic contamination of the isolated RNA was confirmed by performing glyceraldehyde-3-phosphate dehydrogenase (G3PDH) PCR reactions on the purified RNA samples prior to reverse transcription. A negative control of nuclease-free water was included with all sample runs. Each RNA sample was analyzed several times.

V. Immunohistochemical Analysis of Aortic Sinus

Cryostat sections (5 µm thick) of the aortic sinus were evaluated employing indirect immunoperoxidase staining. Slides were than counterstained with Mayer's hematoxylin and mounted with glycerol (Dako). Immunohistochemical staining was performed employing affinity purified goat anti-murine eotaxin-2 (Cytolab, Israel).

Statistical Analysis

Comparison between groups was done by the one-way Anova test. P<0.05 was considered statistically significant. Results are expressed as means and standard error.

Example 1

Specificity and Anti-Inflammatory Effect of an Anti Eotaxin-2 mAb (D8)

Several clones of Anti eotaxin-2 murine monoclonal antibodies (mAbs) were prepared as described above.

The nucleic acid sequence encoding for the D8 antibody heavy chain is denoted as SEQ ID NO:1:

```
GGGCAGCAGANCCGGGGCNGNGGATAGACAGANGGGGGNNGNCGTTTTGGCTGA

GGAGACGGTGACTGAGGTTCCTTGACCCCAGTTGTCCATAGCGTAGCTACTACCGTAGGA

ATGACTTGCACAGAAATATG

TAGCCGTGTCCTCATTTCTGAGGTTGTTGATCTGCAAATAGGCAGTGCTGGCAGAGGTTTC

CAAAGAGAGGGCAAACCGT

CCCTTGAAGTCATCAGTATATGTTGGCTCTCCATTGTAGGTGTTGATCCAGCCCATCCACTT

TAAACCCTTTCCTGGAGC

CTGCTTTACCCAGTTCATTCCAGAGTTTGTGAAGGGATACCCAGAAGCCCTGCAGGAGATC

TTGACTGTGTCTCCAGGCT

TCTTCAGCTCANGTCCAGACTGCACCAACTGGATCTGGGCCATGGCCNGCTA
```

The nucleic acid sequence encoding for the D8 antibody light chain (kappa) is denoted as SEQ ID NO:2:

GGGCCAATGGNNGAGGACGCGGATGGGGGTGTCGNNGTGC

CTTNGTCGNNNNCTNNTTGNNCANCNTCNACNNCNNNNANNNNANNGNNNNNTGNAANA

NNGATGGNNNTNNNCNACANN

NTGGNNTCCTNNNNNNNTNNNNTGNNNNNGACNNCANANACANNNNCNACNNNATGANC

NNCNNNCNNNNNTTGANNNNN

GNCNANTATGAACNANNNAANNNNNNTACCTGNNANGCCACTCACAAGACATCA

The nucleic acid sequence encoding for the G8 antibody heavy chain is denoted as SEQ ID NO:3:

GGGCAGCAGNTCCAGGGGCCAGNGGATAGACAGANGGGGGNGTCGTTTTGGCTG

AGGAGACGGTGACTGAGGTTCCTTGACCCCAGTTGTCCATAGCGTAGCTACTACCGTAGG

AATGACT

TGCACAGAAATAT

GTAGCCGTGTCCTCATTTCTGAGGTTGTTGATCTGCAAATAGGCAGTGCTGGCAGAGGTTT

CCAAAGAGAGGGCAAACCG

TCCCTTGAAGTCATCAGTATATGTTGGCTCTCCATTGTAGGTGTTGATCCAGCCCATCCACT

TTAAACCCTTTCCTGGAG

CCTGCTTTACCCAGTTCATTCCAGAGTTTGTGAAGGGATACCCAGAAGCCCTGCAGGAGAT

CTTGACTGTGTCTCCAGGC

TTCTTCAGCTCAGGTCCAGACTGCACCAACTGGATCTGGGCCATGGCCGGCTANN

The nucleic acid sequence encoding for the G8 antibody light chain (kappa) is denoted as SEQ ID NO:4:

GGGCCAATGGNNGAGGACGCGGATGGGGGTGTCGNNGTGCCT

TNGTCGNGTGCTTNTTGAACAACTTCTACCCCNNANACNTNANNGTNNNNTGGAANATTG

ATGGCNGTGAACGACAAAAT

GGCGTCCTGAACANTTGGACTGATCCANGACAGCAAANACANCNCCTACAGCATGAGCAG

CACCCTCACGTTGACNNNNG

ACNANTNTGAACGACGTANNNNCNNTACCTGTNANGCCACTCACAAGACATCA

The nucleic acid sequence encoding for the G7 antibody heavy chain is denoted as SEQ ID NO:5:

GGGCAGCAGNTCCAGGGGCCAGNNGGATAGACAGANGGGGGNGNCGTTTTGGCT

GAGGAGACGGTGACTGAGGTTCCTTGACCCCAGTTGTCCATAGCGTAGCTACTACCGTAG

GAATGACTTGCACAGAAATA

TGTAGCCGTGTCCTCATTTCTGAGGTTGTTGATCTGCAAATAGGCAGTGCTGGCAGAGGTT

TCCAAAGAGAGGGCAAACC

GTCCCTTGAAGTCATCAGTATATGTTGGCTCTCCATTGTAGGTGTTGATCCAGCCCATCCA

CTTTAAACCCTTTCCTGGA

GCCTGCTTTACCCAGTTCATTCCAGAGTTTGTGAAGGGATACCCAGAAGCCCTGCAGGAG

-continued

```
ATCTTGACTGTGTCTCCAGG

CTTCTTCAGCTCAGGTCCAGACTGCACCAACTGGATCTGGGCCATGGCCGGCTANN
```

The nucleic acid sequence encoding for the G7 antibody light chain (kappa) is denoted as SEQ ID NO:6:

```
GGGCCTTTGGNNGAGGACGCGGATGGGGGTGTCCNNGTGCCT

TNGTCGNGTGCTTNTTGAACAACTTCTACCCCNNANACNTNANNGTNNNNTGGAANATTG

ATGGCNGTGAACGACAAAAT

GGCGTCCTGAACANTTGGACTGATCCANGACAGCAAATACANCNCCTACAGCATGAGCAG

CACCCTCACGTTGACNNNNG

ACNANTNTGAACGACGTANNNNCNNTACCTGTNANGCCACTCACAAGACATCA
```

The letter N in the above nucleic acid sequences designates the presence of either of the nucleotides A, T, C or G.

The hybridoma producing the D8 monoclonal antibody was deposited at the European Collection of Cell Cultures, Salisbury, Wiltshire, UK (ECACC) on Aug. 17, 2009 under the Accession number D809081702.

The hybridoma producing the G8 monoclonal antibody was deposited at the ECACC, on Aug. 17, 2009 under the Accession number G809081701.

The specificity of the novel anti eotaxin-2 antibody (D8) was assessed in a binding assay. Serial dilutions of the mAbs produced in clone D8 were added to plates coated with either eotaxin or eotaxin-2, for an overnight incubation. After washing, the plates were incubated with a goat anti-mouse peroxidase conjugated antibody, washed again and binding was detected using a colorimetric substrate.

Figure 1:
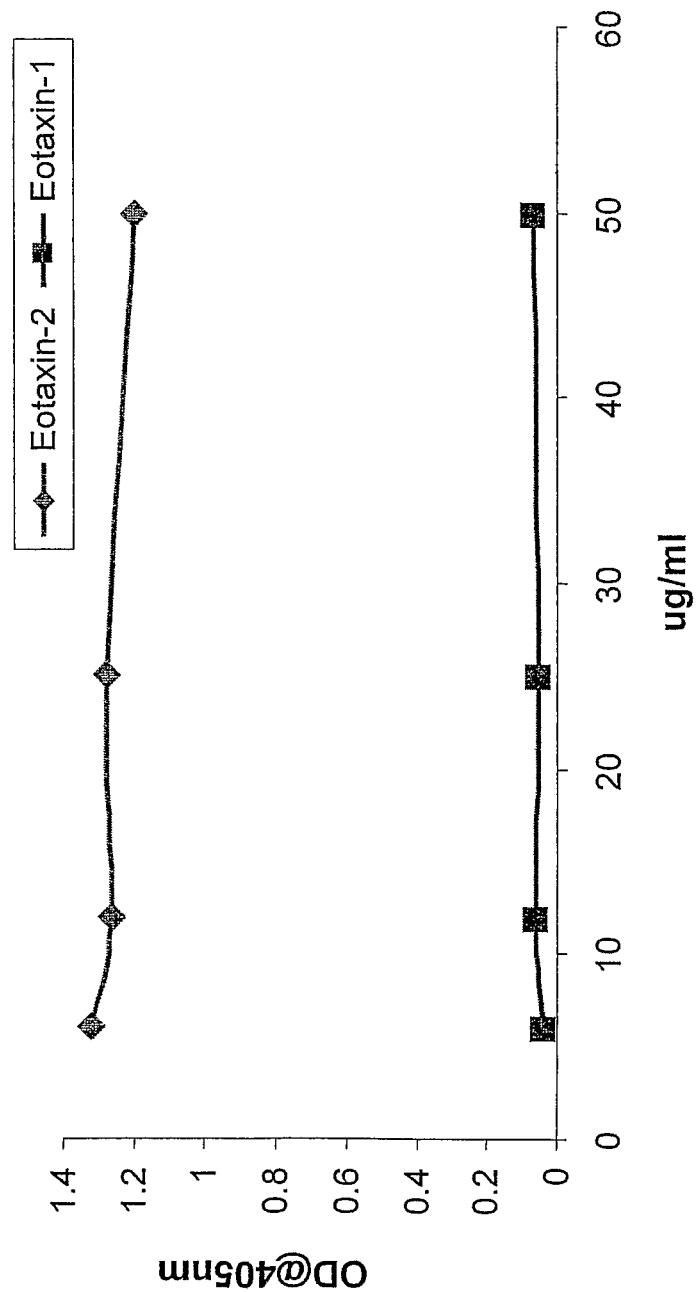
FIG. 1 is a graph showing binding of an anti eotaxin-2 mAb (D8) to eotaxin-2 versus eotaxin. The results are presented as optical density (OD) readings at 405 nm. Various antibody concentrations (between 5µ/ml-50 µ/ml) were measured.

As shown in FIG. 1, mAbs of clone D8 showed significant binding to eotaxin-2 and no binding to eotaxin, in all the range of tested dilutions.

Figure 2A:
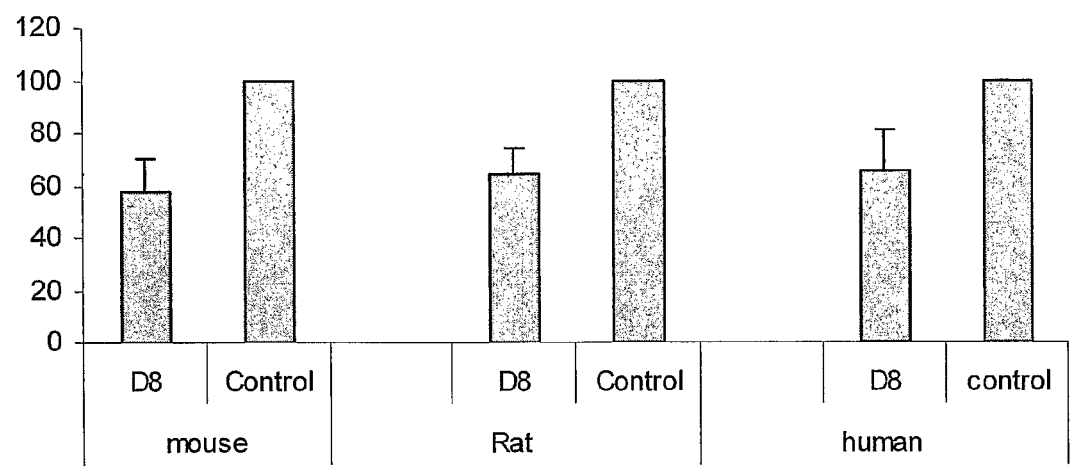
FIG. 2A is a graph showing level of adhesion to fibronectin of D8-treated cells. The results are shown as percent adhesion compared to control cells treated with mouse IgG. Three types of cells were tested, mouse splenocytes, rat splenocytes, and human PBMC.
Figure 2B:
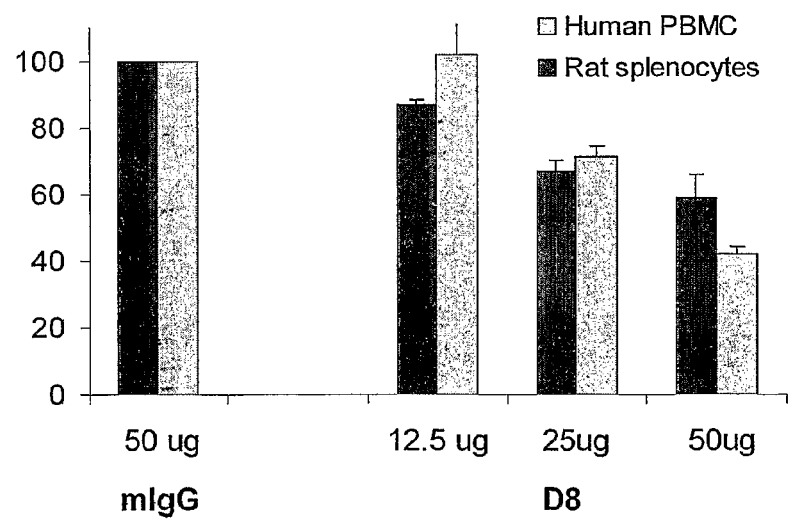
FIG. 2B is a graph showing migration towards VEGF of D8-treated cells. The results are shown as percent migration compared to control cells treated with mouse IgG (50 µg). The graph demonstrates the results obtained with rat splenocytes and human PBMC, using various D8 amounts (12.5, 25 and 50 µg).

The antibodies were also tested for their capability to inhibit adhesion of murine or rat splenocytes as well as human PBMCs to fibronectin or to attenuate their migration towards VEGF. D8 (50 µg) was found to inhibit adhesion of murine and rat splenocytes as well as human PBMC to fibronectin (FN) by 35-55% (FIG. 2A). Migration towards VEGF was also attenuated in a dose-dependant manner (FIG. 2B), confirming the potential anti-inflammatory effects of the antibody.

Example 2

Anti-Inflammatory Potential of Clone D8 mAb (In Vivo Data)

A. Rheumatoid Arthritis Model

Adjuvant arthritis was induced in Lewis rats (six-week-old male Lewis rats obtained from Harlan, Israel) by injection of incomplete Freund's adjuvant. Freund's incomplete adjuvant was prepared by suspending heat-killed *Mycobacterium Tuberculosis* (Difco, Detroit, Mich.) in mineral oil at 10 mg/ml. Rats were injected intradermally with 100 µl adjuvant at the base of the tail. Arthritis developed by day 10 post injection.

Evaluation of the Effect of Anti-Eotaxin-2 Antibodies, Compared with Nonspecific IgG and PBS as Controls, on Adjuvant Induced Arthritis:

Rats (8 per group) were treated by intraperitoneal (IP) injection with 3 monoclonal antibodies against eotaxin-2, (G7, G8, D8) 3×/week. Controls were treated with total mouse (non specific) IgG or PBS. Injections were started on the third day after adjuvant administration and were performed three times a week until the rats were sacrificed.

Dose Response Experiments:

In a second set of experiments, D8, the anti-eotaxin-2 antibody showing best protective results in the adjuvant-induced arthritis model, was tested in a dose-response model. Adjuvant arthritis was induced according to the above described protocol. Animals (6 rats per arm) were treated with D8 intraperitonealy at a dose of 20 µg, 100 µg or 1000 µg, starting on day 3 after adjuvant injection, three times weekly (D8 prevention group). A separate set of animals (6 in each group) were treated with identical doses after arthritis onset, namely when arthritis was already evident (D8 treatment group).

In order to compare the anti-inflammatory efficacy of D8 with that of a traditional anti-inflammatory agent of known efficacy, one group was treated with methotrexate (ip), 0.25 mg/kg, once weekly, starting on day 3 after adjuvant injection (methotrexate prevention group). An additional group was treated with methotrexate, 0.25 mg/kg once weekly, in combination with D8, 100 µg (ip injection) given 3 times a week, starting on day 3 (combined D8-methotrexate prevention group). A control group was treated with PBS throughout the experiment.

Evaluation of Arthritis Severity:

Arthritis severity was evaluated by measuring body weight, paw swelling, arthritic score and whole animal mobility. Sample joints were obtained for pathological evaluation, and post mortem X-ray of ankle joints was performed to document erosions.

Body weight in grams was measured every other day as an indicator of systemic inflammation.

Evaluation of Paw swelling. Ankle and wrist diameter in mm (to one place after the decimal point) were recorded three times a week using a caliper.

Arthritic score measurement: Each paw was scored on a scale of 0-4 for the degree of swelling, erythema, and deformity (maximum score 16 per animal accounting for all four paws) as follows: 0=normal; 1=slight erythema and/or swelling of the ankle or wrist; 2=moderate erythema and/or swelling of ankle or wrist; 3=severe erythema and/or swelling of ankle or wrist; 4=complete erythema and swelling of toes or fingers and ankle or wrist, and inability to bend the ankle or wrist.

Finger and toe swelling was recorded according to their partial contribution: Ankles (feet): each toe scored 0.2; Wrist: each finger scored 0.25 Sum of all joints was calculated.

Mobility Score:

Whole animal Mobility was scored between 0-4, according to the following definitions:

0=normal; 1=slightly impaired; 2=major impairment; 3=does not step on paw; 4=no movement.

Statistical Analysis:

QuickCalcs software (Graph-Pad Software, San Diego, Calif.) was used for statistical analysis. Student's t-test was performed to identify significant differences between experimental groups.

Results

A. Arthritis Model

Figure 3A:
FIG. 3A is a graph showing the effect of treatment with anti-eotaxin-2 monoclonal antibodies (G7, G8, D8), IgG and PBS on the arthritic score (AS) of rats standard error) as a function of time from onset of the disease. Day zero is the day of arthritis induction.
Figure 3B:
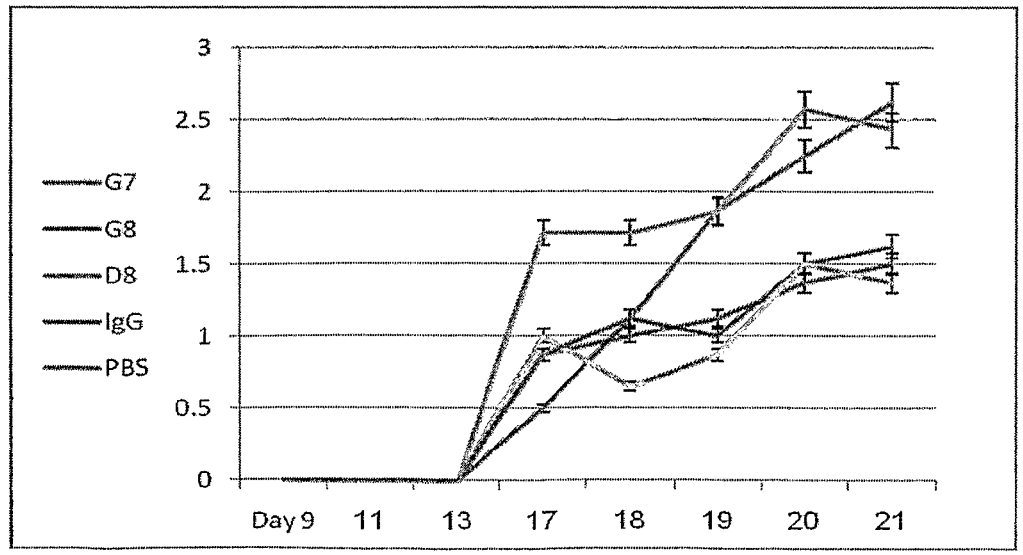
FIG. 3B is a graph showing the effect of treatment with anti-eotaxin-2 monoclonal antibodies (G7, G8, D8), IgG and PBS on the mobility score of rats (±standard error).
Figure 3C:
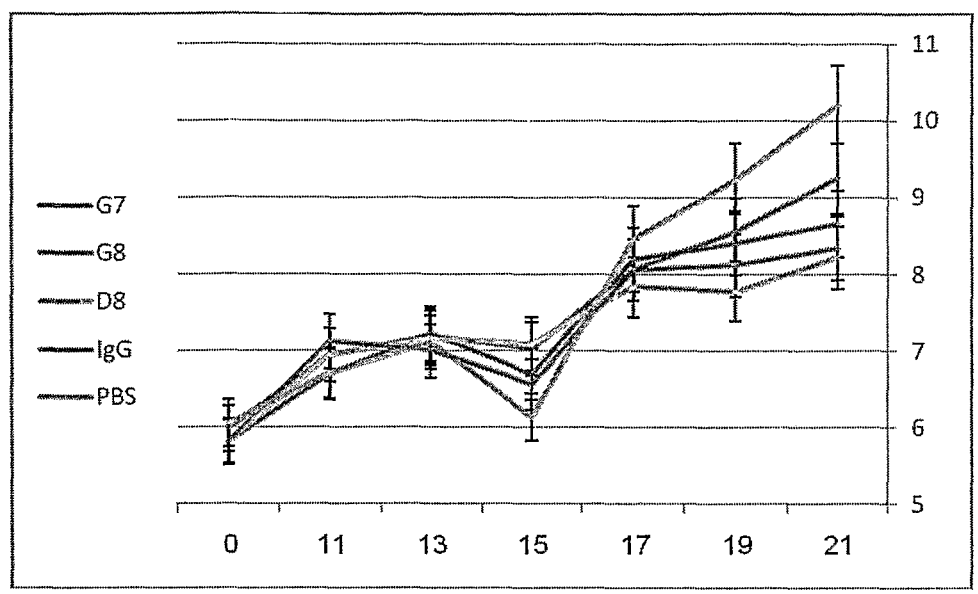
FIG. 3C is a graph showing the effect of treatment with anti-eotaxin-2 monoclonal antibodies (G7, G8, D8), IgG and PBS on ankle diameter (mm) (±standard error)

Significant inhibition of arthritis was observed in rats treated with the anti-eotaxin-2 antibodies, compared to those treated with immunoglobulin (IgG) or PBS. As demonstrated in FIGS. 3A-3C, inhibition by the antibodies was manifested in all the tested parameters (arthritic score, mobility score, and ankle diameter). The antibody marked D8 showed the most significant effect. In the arthritic score test (FIG. 3A) statistically significant differences ($P<0.05$) were obtained at every measurement, from day 13 to day 21, when comparing rats treated with D8 to rats treated with PBS or to rats treated with IgG. The protective effect became evident immediately with appearance of arthritis, on day 17 after induction. It continued to increase in magnitude until the end of the experiment, on day 21.

In the mobility score test statistically significant differences ($P<0.05$) were obtained at every measurement, from day 17, when comparing rats treated with D8 to rats treated with PBS, and from day 18 when comparing rats treated with D8 to rats treated with PBS or to rats treated with IgG. Thus, the average mobility score of animals treated with D8 was 1.37 on day 21 compared with 2.43 in animals treated with PBS ($p=0.05$).

In the ankle diameter tests statistically significant difference ($p<0.05$) was obtained between D8 and PBS as of day 19. The difference between D8 and IgG did not reach statistical significance.

Figure 4A:
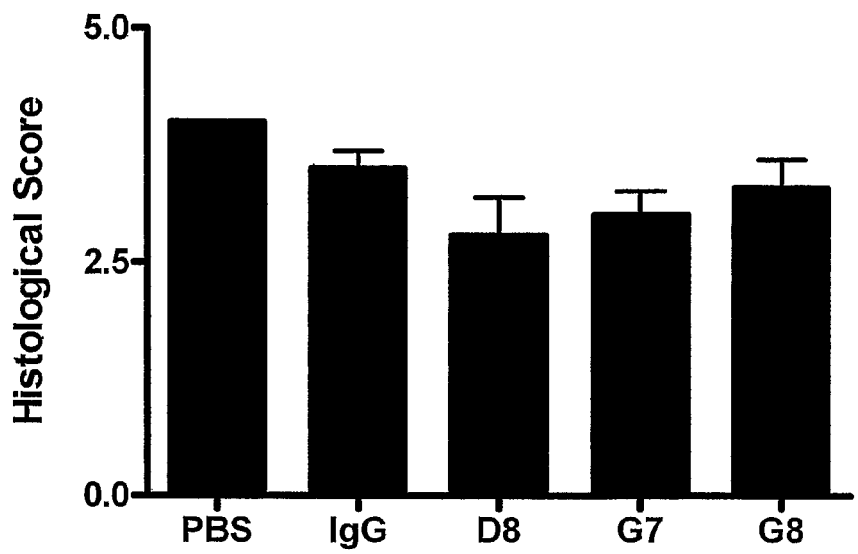
FIG. 4A is a graph showing histological scoring of joints from rats treated with PBS, IgG, D8, G7 and G8 antibodies.
Figure 4B:
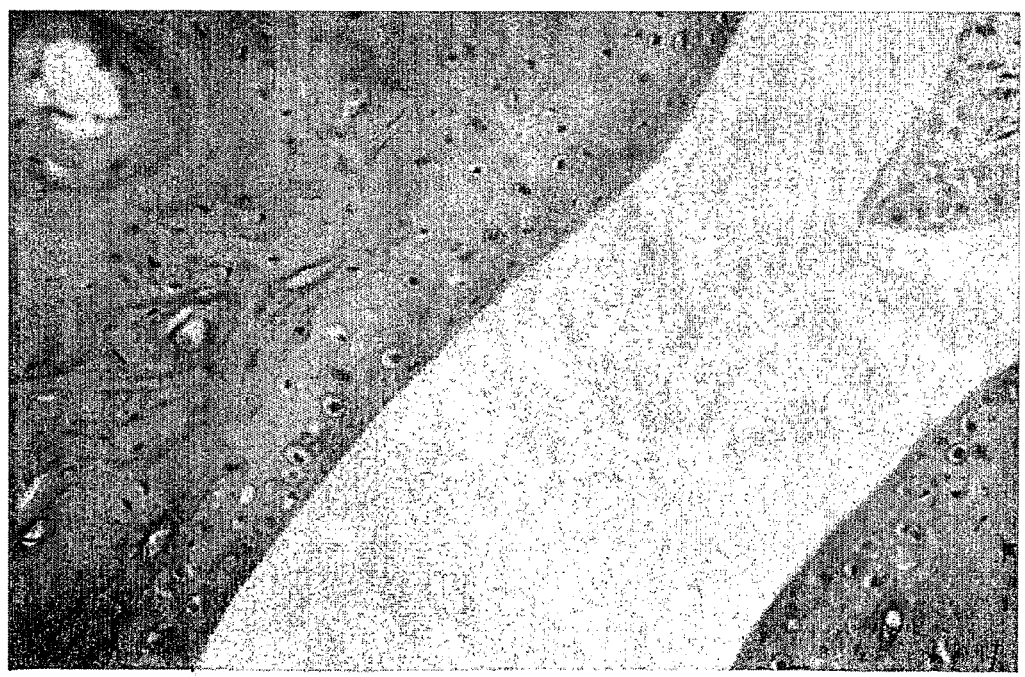
FIGS. 4B and 4C are photographs showing representative appearance of joints from rats treated with D8 (FIG. 4B) or PBS (FIG. 4C) (hematoxylin eosin (H&E) staining).
Figure 4C:

As indicated above, D8 treated rats had lower scores of arthritis which ranged from 2.6 to 3.0 than rats treated with PBS (FIG. 4A). For the histological scoring, each paw was scored on a scale of 0-4 for the degree of destruction: 0=normal; 1=inflammatory infiltrates and synovial hyperplasia; 2=pannus formation and cartilage erosion; 3=important cartilage erosion and bone destruction; 4=loss of joint integrity. Histological analysis of the joints of the arthritic rats revealed that joints of D8 treated rats had synovial hyperplasia and scattered inflammatory infiltrates (FIG. 4B), while most of the rats treated with PBS (control group) had severe synovitis with panus formation and an intense inflammatory infiltrate (FIG. 4C).

Figure 5:
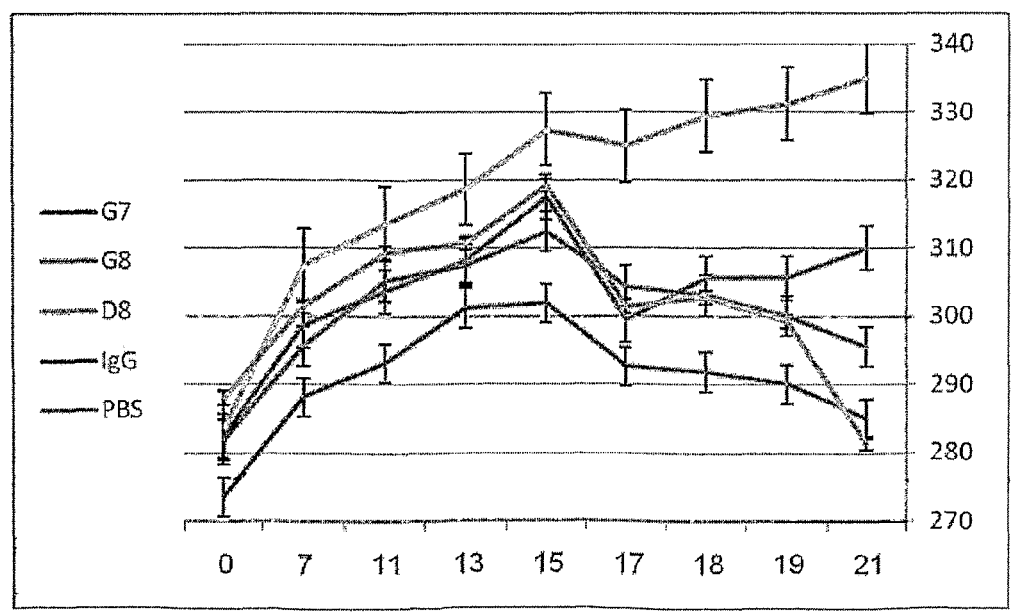
FIG. 5 is a graph showing the effect of treatment with anti-eotaxin-2 monoclonal antibodies (G7, G8, D8), IgG and PBS on weight (in grams) of rats with adjuvant induced arthritis (±standard errors), as a function of time (days).

In order to evaluate the effect of treatment with anti-eotaxin-2 antibodies on the systemic inflammatory response, average weight of animals was documented. As shown in FIG. 5, anti-eotaxin-2 treatment significantly ameliorated the loss of weight caused by the systemic inflammatory response induced by adjuvant arthritis. Again, the maximal protective effect was observed in animals treated with the D8 antibody, which continued to gain weight throughout the experiment. Statistically significant difference in weight ($p<0.05$) between D8 and PBS was obtained on day 17.

Figure 6A:
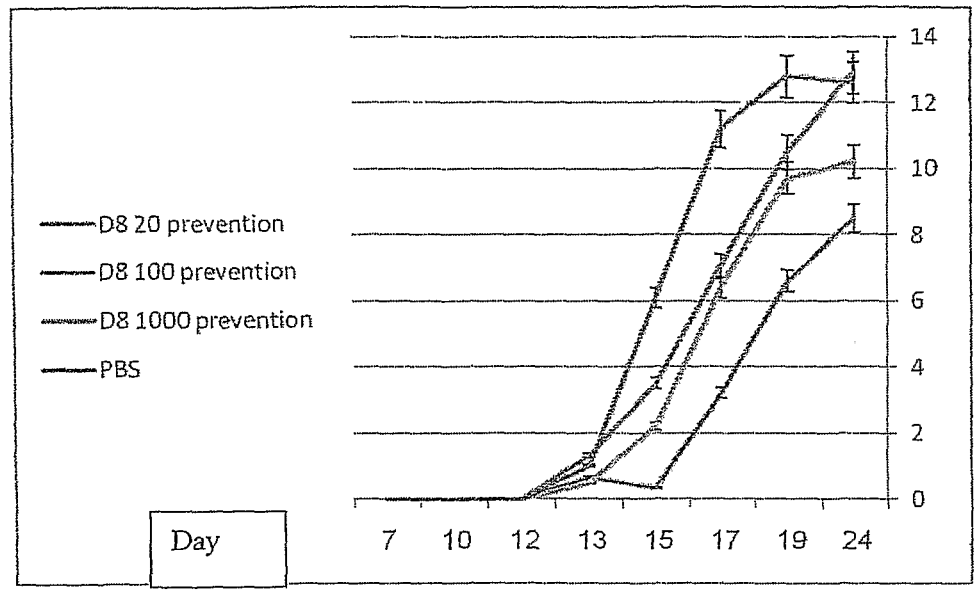
FIG. 6A is a graph showing the effect of the anti-eotaxin-2 D8 antibody in a prevention mode at three doses (20 µg, 100 µg and 1000 µg) on the arthritic score (AS; Y axis) in adjuvant induced arthritis (±Standard error, percentage), as a function of time (days).

Dose Response Experiments:

D8 Prevention of Arthritis:

In the series of dose response experiments, D8 at a dose of 100 µg had a significantly superior protective effect, compared with the low dose (20 µg) and high dose (1000 µg) groups (FIG. 6A). Similar results were obtained regarding the mobility scores, ankle diameter and animal weight (data not shown). Statistically significant differences ($P<0.05$) were obtained at every determination, from day 17 to day 24 when comparing rats treated with D8 100µ to rats treated with PBS.

Figure 6B:
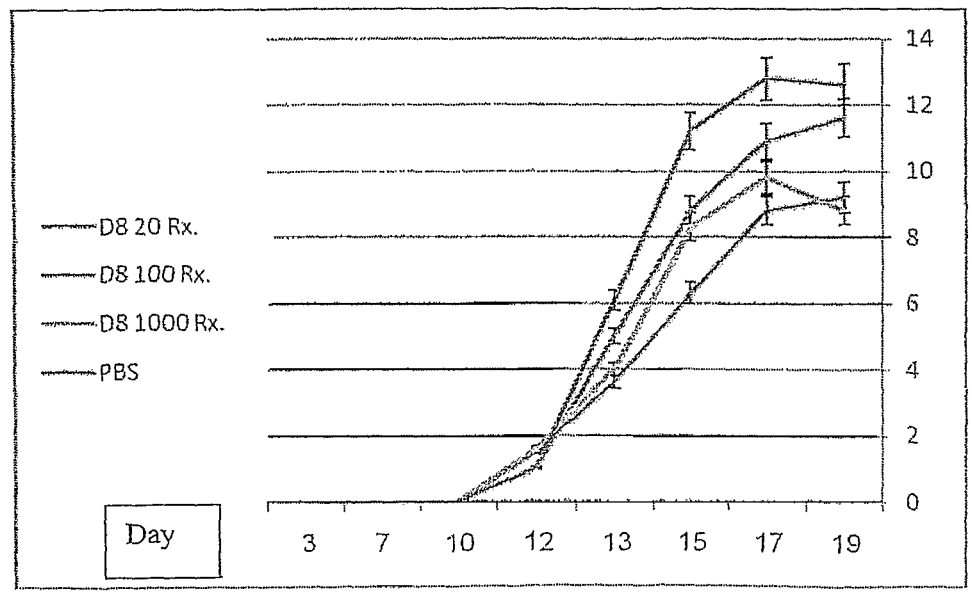
FIG. 6B is a graph showing the effect of the anti-eotaxin-2 D8 antibody in a treatment mode (administration with the appearance of arthritis) at three doses (20 µg, 100 µg, and 1000 µg) on the arthritic score (AS; Y axis) in adjuvant induced arthritis (±Standard error), as a function of time (days).

D8 Treatment of Arthritis:

Treatment with D8 Antibody Intraperitonealy Beginning at the Time of appearance of arthritis also resulted in a significant reduction in arthritic score severity (FIG. 6B) compared with PBS treated animals. Similar results were obtained regarding mobility, weight and ankle diameter. As demonstrated in FIG. 6B, in this experimental set up similar results were obtained at the 100 µg and 1000 µg dose groups.

Figure 7:
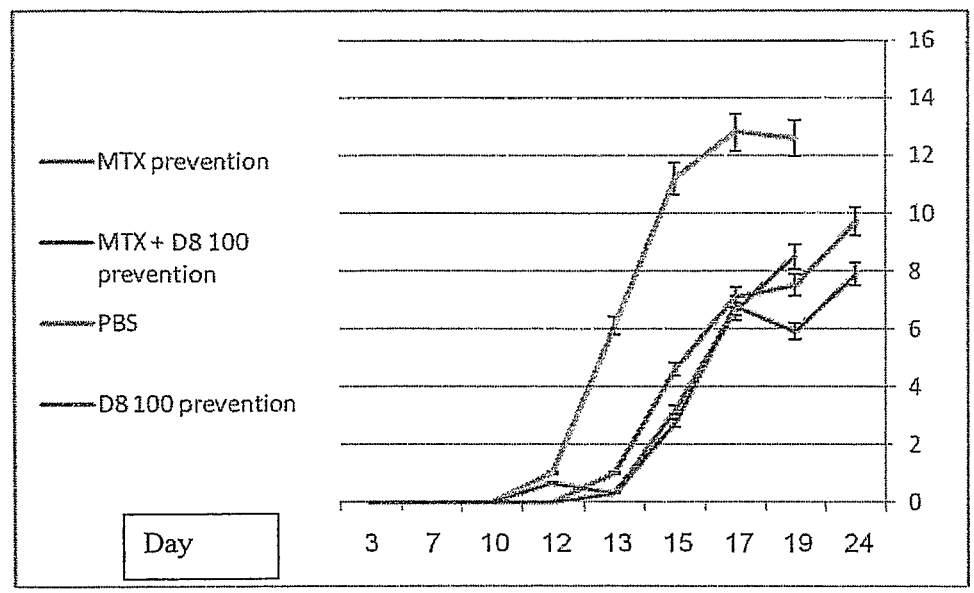
FIG. 7 is a graph showing the protective effect of D8 (100 µg), methotrexate (0.25 mg/kg) and methotrexate combined with D8 100 µg, compared with PBS-treated control, on the arthritic score in adjuvant induced arthritis in a prevention mode (±Standard error) as a function of time (days).

Combined D8-Methotrexate (MTX) Prevention of Arthritis:

While both methotrexate and D8 100 µg produced significant, comparable protection against development of arthritis, as measured by the arthritic score (compared to PBS treated controls), the combination of methotrexate and D8 produced an enhanced (synergistic) protective effect, as demonstrated in FIG. 7.

Both D8 100 µg and MTX treatment caused a statistically significant effect ($p<0.05$) compared with PBS as of day 13. By the end of the experiment, on day 24, a statistically significant difference in the arthritis score was observed between rats treated with MTX alone and rats treated with MTX+D8 100 µg. A significant difference was also observed on day 24 in the mean ankle width between these groups (not shown).

Figure 8A:
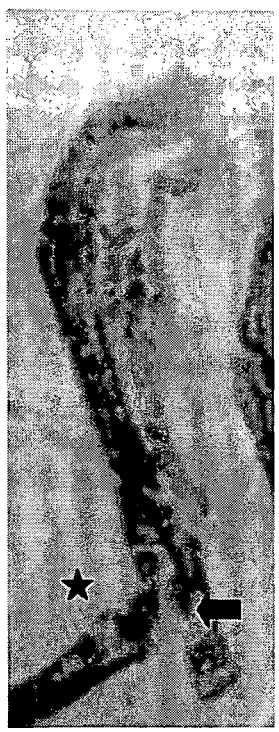
FIG. 8 is a photograph of a post-mortem x-ray analysis of joints from rats treated with PBS (FIG. 8A) and D8 (FIG. 8B). Intense periarticular soft tissue swelling is evident in the PBS treated rats (star), as well as decalcification and early boney erosion at the ankle joint (arrow head) (Representative figures).
Figure 8B:
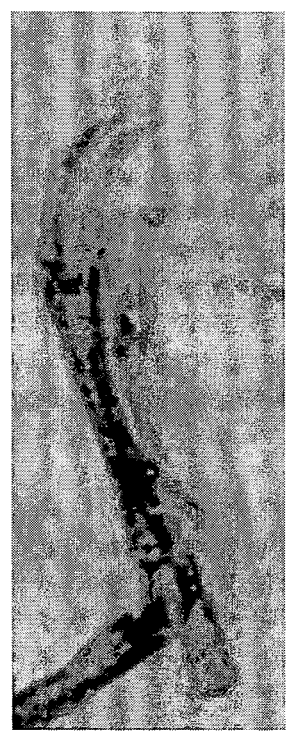

X-Ray Results:

Post-mortem X-ray demonstrated an intense degree of peri-articular soft tissue swelling in PBS treated rats, compared with minimal swelling in rats treated with D8 (FIG. 8). In addition, control rats showed signs of decalcification and early erosion, which was not evident in the D8 treated animals. This is indicative of a significant reduction of inflammation in D8 treated animals.

Similar results were seen in x-rays of the forefeet (not shown).

B. Colitis Model

In order to induce chronic colitis, ten-week old C57BL mice underwent three cycles of exposure to dextrane sulfate (DSS) in their drinking water for five days followed by 10-day intervals with regular tap water. By the end of the first cycle, mice were randomized into six treatment arms: vehicle control (PBS), total mouse IgG, and D8 given at increasing doses of 5 µM, 25 µM, 100 µM and 200 µM. Treatment was given by intraperitoneal (ip) injection in a 3×/week regimen. Body weight was documented twice a week. By the end of the last cycle, mice were sacrificed; the proximal portions of the colon were taken for immunohistochemical analysis and the distal portion for myeloperoxidase (MPO) activity assay (according to standard protocols) in order to assess the degree of the induced inflammation. The levels of inflammatory cytokines in the animals' sera were detected by flow cytometry.

Figure 9A:
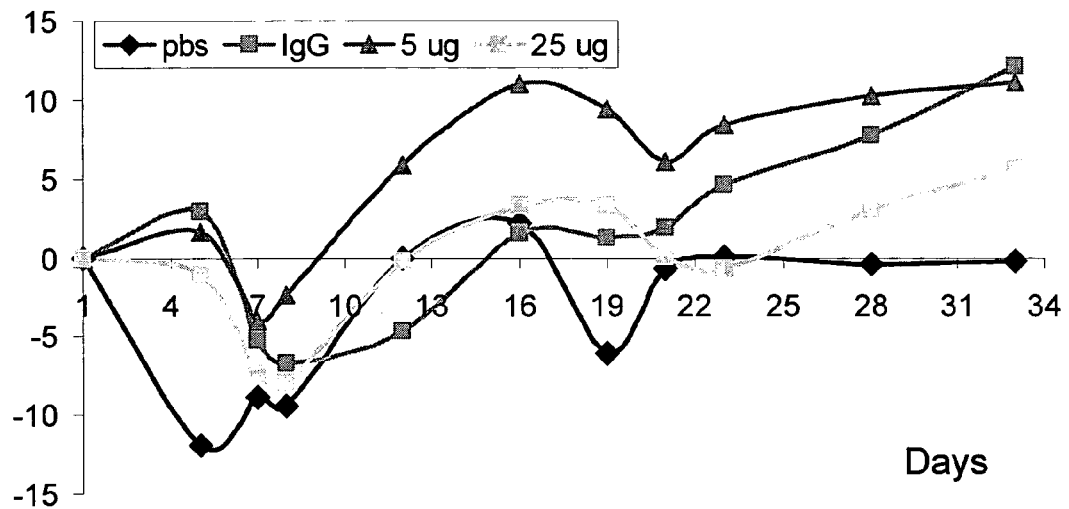
FIG. 9A is a graph demonstrating percent weight loss/gain in mice with DSS-induced colitis as a function of time (days). The mice were treated with 5µ or 25µ of the anti eotaxin-2 antibody D8. Control animals were treated with PBS or IgG.
Figure 9B:
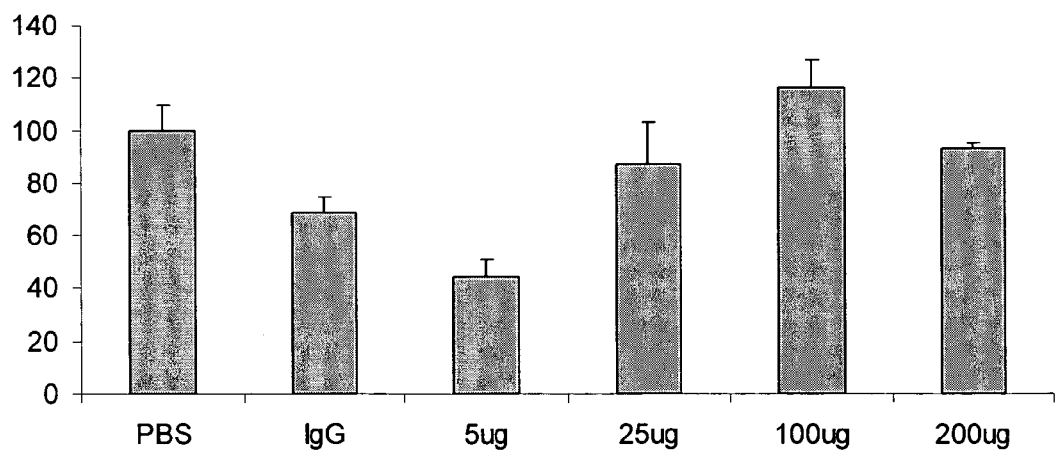
FIG. 9B is a graph demonstrating % MPO activity in mice with DSS-induced colitis. The mice were treated with 5µ, 25µ, 100 µg or 200 µg of the anti eotaxin-2 antibody D8. Control animals were treated with PBS or IgG.
Figure 9C:
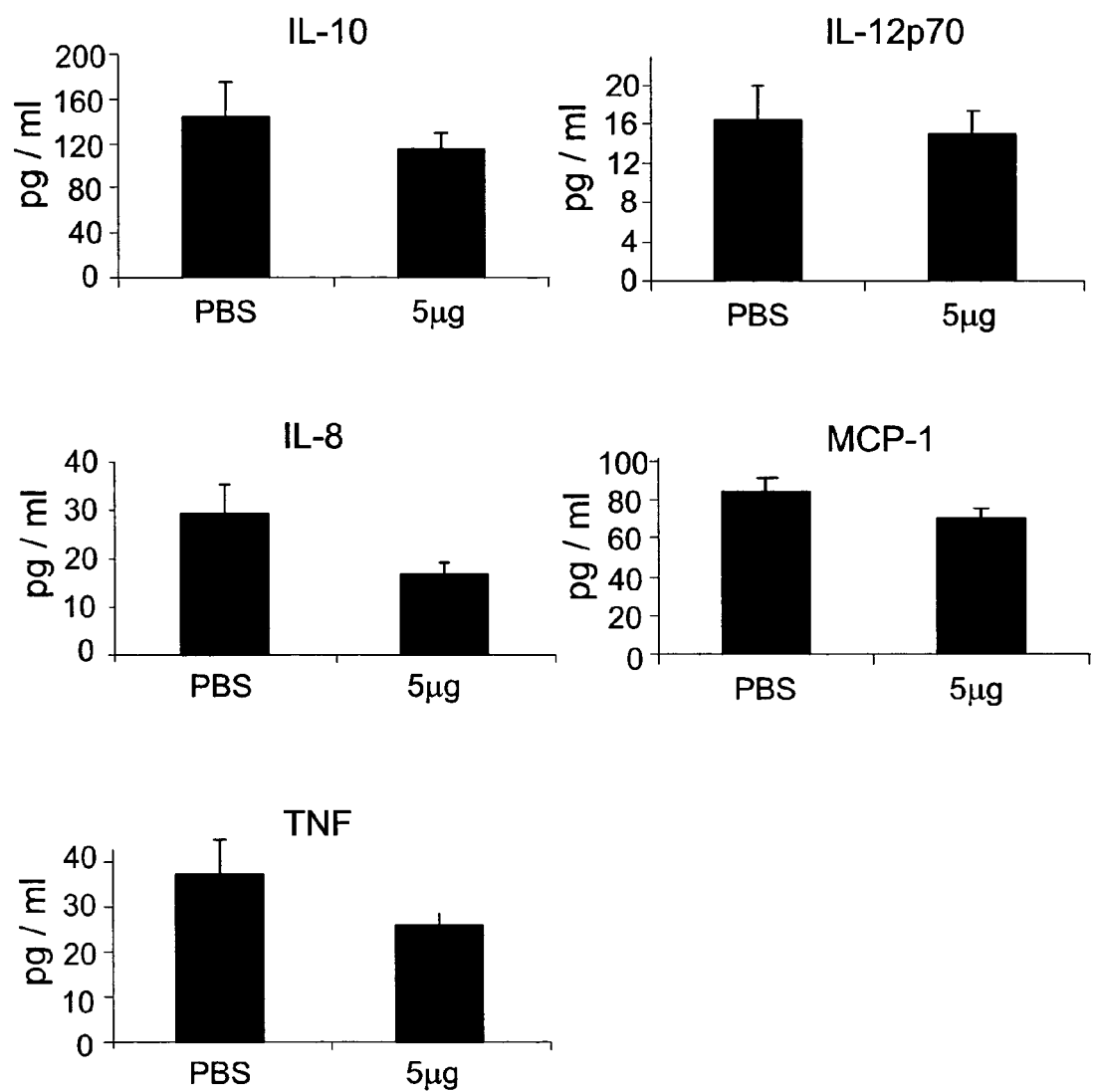
FIG. 9C is a graph demonstrating the level of various cytokines (IL-10, IL-12p70, IL-6, MCP-1 (monocyte chemoattractive protein-1) and TNF) in the sera of mice with DSS-induced colitis treated with either anti-eotaxin-2 antibody D8 (5 µg) or control (PBS).
Figure 9D:
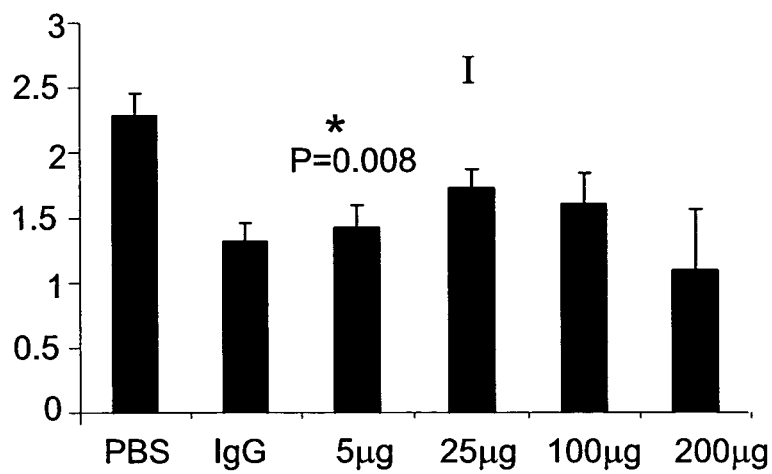
FIG. 9D is a graphical representation of histological analysis of colons of mice with DSS-induced colitis treated with 5µ, 25µ, 100 µg or 200 µg of the anti eotaxin-2 antibody D8.
Figure 9D:
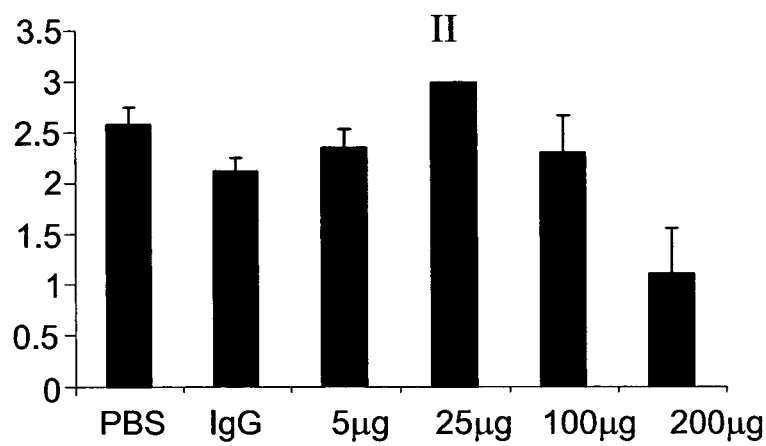
Figure 9D:
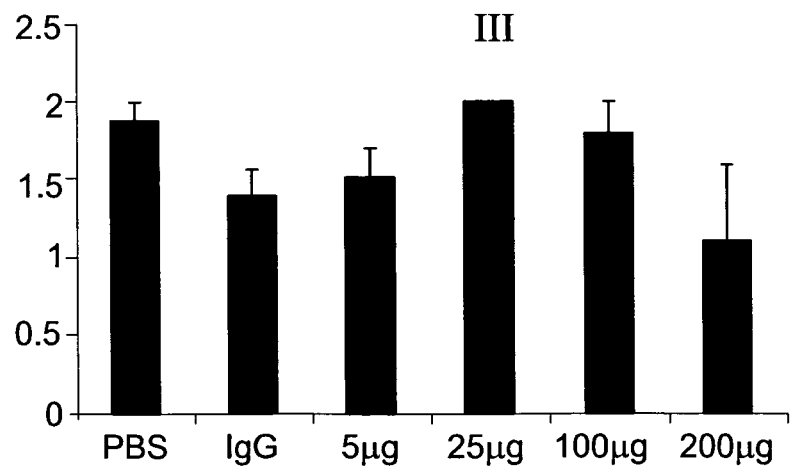

Treatment with IgG or with D8 significantly attenuated body weight loss compared to vehicle-treated animals. Throughout the study, the highest body weight was observed in the 5 µg D8 treatment arm (FIG. 9A). MPO activity on day 34 was significantly reduced in the 5 µg D8 treatment group compared to all other treatment arms including mIgG (FIG. 9B). In addition, the level of inflammatory cytokines in the sera of the D8-treated animals was lower than that detected in control animals (FIG. 9C). Immunohistochemical analysis of the proximal colon confirmed reduction in the level of damage to the colon tissue as well as reduction in the extent and degree of inflammation (FIG. 9D). The extent of inflammatory infiltrate was evaluated by an expert pathologist.

C. EAE

EAE serves as a typical animal model to study potential therapeutics for the human disease multiple sclerosis (30).

Ten-week old C57BL mice were injected subcutaneously (sc) with 200 µg MOG (Myelin Oligodendrocyte Glycoprotein) peptide suspended in Complete Freund's adjuvant, followed by a second injection one week later. One day after induction of the disease (namely, one day after the second injection) treatment with vehicle control (PBS), total mouse IgG, 25 µg D8 and 100 µg D8 (3×/week, ip injections) commenced. The severity and the progression of the disease was documented 3×/week according to the standard EAE scoring system (31).

Treatment with 25 µg, and more significantly with 100 µg of D8, attenuated the progression of EAE signs during the whole course of the experiment. Moreover, D8 at the higher dose (100 µg) reduced the incidence of the disease from about 90% (in all other treatment groups) to only 55% (FIG. 10), thus shedding light on the potential therapeutic advantage of D8 in the treatment of EAE.

D. Diabetes

The non-obese diabetic (NOD) mouse serves as an animal model of autoimmune diabetes (32).

Six-week old NOD mice were treated 3×/week with D8 or with vehicle control (PBS). Between days 49 to 112, the disease incidence was tested using a commercial urine test and the eotaxin-2 levels in their sera on day 112 was determined using an ELISA (Mouse CCL24/eotaxin-2/MPIF-2 DuoSet; R&D).

Diabetic incidence was markedly reduced in the D8-treated group compared to the untreated control (FIG. 11A). In line with the clinical improvement, the level of eotaxin-2 was greatly reduced in the sera of the anti-eotaxin-2-treated animals compared to the control ones (FIG. 11B).

E. Inhibition of Atherosclerotic Plaque Formation

The expression level of an array of inflammatory cytokines and chemokines was measured in atherosclerotic lesions (plaques). Vulnerable plaques recovered from culprit coronary arteries of patients with acute myocardial infarction were compared with stable plaques obtained from endarterectomy samples. An analysis of the plaques by protein arrays is shown in FIG. 12. Processing was done as described in the materials and methods section.

Among the differentially expressed proteins, a significant alteration was found in the following proteins: VCAM-1, eotaxin-2, IL-10, MCP-1 and TIMP-2; all exhibited a more than twofold reduction in expression in vulnerable versus stable plaques (FIG. 12A).

In immunohistochemistry studies in atherosclerosis prone mice (apoE KO mice), fatty streaks and advanced lesions from young and older mice were stained with anti-eotaxin-2 abs as described in materials and methods. Eotaxin-2 was shown to be present within endothelial cells and within plaque macrophages (FIG. 13).

mRNA expression was measured in young (6 week old) and atherosclerotic apoE KO mice. Aortas were obtained from the mice and subjected to RT-PCR as described in materials and methods. mRNA levels of eotaxin-2 and TGF-beta were assayed comparatively. Eotaxin-2 mRNA levels were found to be significantly higher in the young versus the older mice and this expression pattern paralleled the one observed with regard to the anti-atherosclerotic agent TGF-beta. FIG. 14A shows representative examples from each group.

Oxidized LDL is considered to play a key role in promoting atherogenesis. Mouse H5V endothelial cells were incubated with oxidized LDL (oxLDL) (1 µg/ml). oxLDL significantly upregulated eotaxin-2 mRNA levels in murine H5V endothelial cells (FIG. 14B).

To determine whether eotaxin-2 has a role in the adhesion of cellular components of plaque inflammation, adhesion assays were performed on cultured endothelial cells. Splenocytes from either young or older atherosclerotic apoE KO mice were isolated from the spleen. Murine endothelial cells were incubated with oxLDL (1 µg/ml) and the adhesion of the splenocytes onto the endothelial cells was examined in the presence of eotaxin 2 or control IgG antibodies (FIG. 15A). Preincubation of the endothelial cells with blocking antibodies to eotaxin-2 was found to attenuate the adhesion of the splenocytes to these cells (FIG. 15A). This effect was more robust in lymphocytes from atherosclerotic (6 months old) apoE KO mice compared to those obtained from young non-atherosclerotic mice (aged 6 weeks). These findings were also evident when monocyte-macrophage cell line (U937 cells) was allowed to adhere to the cultured endothelial cells (H5V murine endothelial cell line) (FIG. 15B).

The effect of eotaxin-2 blockade on early and advanced atherosclerotic plaques was measured using commercially available anti eotaxin-2 antibodies as well as the monoclonal antibodies of the invention. In preliminary studies, it was found that administration of twice weekly doses of 5 µg of blocking anti-eotaxin-2 antibodies (Peprotech) were sufficient to significantly reduce eotaxin-2 mRNA levels in the aortas of the mice. Next, the effect of short term administration of anti-eotaxin-2 abs was examined. Young apoE KO mice were treated with Eoaxin-2 antibodies twice a week (i.p injections of 5 µg), or with control IgG or with PBS for 4 weeks and the effect on fatty streaks was measured. The mice were sacrificed for analysis of plaque size after oil-red O staining. Anti-eotaxin-2 drastically reduced fatty streak formation as compared to mouse IgG by approximately 72 percent (FIG. 16A). This effect was not associated with a change in lipid profile as total cholesterol and triglycerides were similar in both groups (data not shown). Moreover, treatment with control murine IgG did not influence plaque progression in comparison with PBS injections.

Next the effects of eotaxin-2 blockade were tested in a long-term model in which plaque architecture is more complex. Herein, after 10 weeks of two weekly injections of eotaxin-2 antibodies (5 µg/dose), no significant differences were evident with regard to plaque size as measured in the hearts of older apoE KO mice (FIG. 16B). However, when plaque stability measured by fibrous area was assayed, it was found that antibodies to eotaxin-2 induced a significantly more stable plaque phenotype evident by a larger fibrous area at the expense of a smaller lipid core (FIG. 16C). Again, these findings were irrespective of lipid levels that were not different between groups. Representative Oil-red O and masson's trichrome stained sections are provided in FIG. 17.

Atherosclerosis is a process in which fat deposition progresses in the arterial wall leading to progressive narrowing of the lumen. The mature plaque is composed of two basic structures: the lipid core and the fibrous cap. The smaller the lipid core and the thicker the fibrous cap, the more stable the plaque is, meaning that its propensity to rupture and cause myocardial infarction or unstable angina are decreased. It is now clear that most plaques that cause acute coronary syndromes (e.g., myocardial infarction and unstable angina) are angiographically shown to have <70% stenosis (reviewed in 28, 29). Approximately 60% of these lesions are caused by rupture of plaques with a large thrombogenic core of lipid and necrotic debris (including foci of macrophages, T cells, old hemorrhage, angiogenesis, and calcium). The ruptured cap is thin, presumably because macrophages secrete matrix metalloproteinases that digest it as they move across plaque, and because smooth muscle cells (the supporting element of the plaque) are depleted due to senescence or apoptosis caused by several factors, such as inflammatory cytokines.

In one of its aspects, the present invention is based on the finding that eotaxin-2 is differentially expressed in stable versus vulnerable human atherosclerotic plaques. By blocking the eotaxin-2 pathway in an apoE knockout (KO) [20] mouse model, the inventors were able to demonstrate both inhibition of fatty streak formation (which signifies early atherosclerotic lesions) and prolongation of plaque stabilization.

The inventors of the present invention found that eotaxin-2 is expressed in the endothelium of atherosclerotic and non atherosclerotic murine arteries supporting previous reports in the art. However, the inventors have also found that eotaxin-2 is expressed in plaque macrophages. Eotaxin-2 was more abundantly expressed in the aortas of young apoE KO mice as compared to atherosclerotic apoE KO mice. Suggesting that eotaxin-2 is involved in the initial steps of atherosclerosis that comprise cell to cell adhesion of monocytes/macrophages to the endothelium. Indeed, the in-vitro studies described below show that blocking eotaxin-2 reduces oxLDL induced adhesion of lymphocytes to endothelial cells, supporting a role for eotaxin-2 in plaque formation in vivo.

Despite intensive research, the factors that govern the transition of a stable to vulnerable plaque remain elusive. Based on an inflammatory protein array analysis of stable versus vulnerable human plaques, the present invention provides a potential target protein, eotaxin-2, to be involved in the transition of the plaque between a stable and a vulnerable phenotype. Whereas solid data exists with respect to the association of atherosclerosis with VCAM-1, IL-10 and MCP-1, which were also found by the inventors to be differentially expressed in stable versus vulnerable plaques, no such data exists for eotaxin-2.

In addition, eotaxin-2 was found by the inventors to be expressed in the endothelium of atherosclerotic and non atherosclerotic murine arteries thus supporting previous reports. However, it was also found by the inventors to be expressed in plaque macrophages. Interestingly, eotaxin-2 was more abundantly expressed in the aortas of young versus atherosclerotic apoE KO mice corresponding to initial steps of atherosclerosis that comprise cell to cell adhesion of monocytes/macrophages to the endothelium. Indeed, the in-vitro studies support a role for eotaxin-2 blockade in oxLDL mediated adhesion as may well occur in vivo. The more robust expression of eotaxin-2 in early stages of murine atherosclerosis also explains the impressive effect of blocking this pathway in the short term fatty streak model. Without wishing to be bound by theory, blocking inflammatory cell adhesion to the endothelium may be principally responsible for this effect.

With respect to the effects of eotaxin-2 blockade on plaque stability as evident by fibrous area, if inflammatory cell recruitment is attenuated due to eotaxin-2 blockade, it may be anticipated that the cytokine milieu will be more favorable towards a stable phenotype. These findings may not necessarily be reflected in a reduced extent of atherosclerosis as plaque built up is more likely to be influenced by lipid profile that has not changed due to eotaxin-2 blockade.

REFERENCES

1. Viola A L A. Chemokines and their receptors: drug targets in immunity and inflammation. Annu Rev Pharmacol Toxicol 2008; 48:171-97.
2. Jose P J, Griffiths-Johnson D A, Collins P D et al., Eotaxin: a potent eosinophil chemoattractant cytokine detected in a guinea pig model of allergic airways inflammation, J Exp Med 1994; 179: 881-887.
3. Kitaura M, Nakajima T, Imai T, et al., Molecular cloning of human eotaxin, an eosinophil-selective CC chemokine, and identification of a specific eosinophil eotaxin receptor, CC chemokine receptor 3, J Biol Chem 1996; 271: 7725-7730.
4 Ponath P D, Qin S, Ringler D J, et al., Cloning of the human eosinophil chemoattractant, eotaxin. Expression, receptor binding, and functional properties suggest a mechanism for the selective recruitment of eosinophils. J Clin Invest 1996; 97: 604-612.
5. Bocchino V, Bertorelli G, Bertrand C P, et al., Eotaxin and CCR3 are up-regulated in exacerbations of chronic bronchitis, Allergy 2002; 57: 17-22.
6. Romagnani P, Annunziato F, Lasagni L, Lazzeri E, Beltrame C, Francalanci M, Uguccioni M, Galli G, Cosmi L, Maurenzig L, et al. Cell cycle-dependent expression of CXC chemokine receptor 3 by endothelial cells mediates angiostatic activity. J. Clin. Invest. 2001; 107:53.
7. Berger O, Gan X, Gujuluva C, Burns A R, Sulur G, Stins M, Way D, Witte M, Weinand M, Said J, Kim K S, Taub D, Graves M C, Fiala M. CXC and CC chemokine receptors on coronary and brain endothelia. Mol. Med. 1999; 5: 795-805.
8. Cheng S S, Lukacs N R, Kunkel S L. Eotaxin/CCL11 suppresses IL-8/CXCL8 secretion from human dermal microvascular endothelial cells, J Immunol 2002; 168 2887-2894.
9. Salcedo, R., J. H. Resau, D. Halverson, E. A. Hudson, M. Dambach, D. Powell, K. Wasserman, J. J. Oppenheim. 2000. Differential expression and responsiveness of chemokine receptors (CXCR1-3) by human microvascular endothelial cells and umbilical vein endothelial cells. FASEB J. 14:2055.
10. Salcedo, R., H. A. Young, M. L. Ponce, J. M. Ward, H. K. Kleinman, W. J. Murphy, J. J. Oppenheim. 2001. Eotaxin (CCL11) induces in vivo angiogenic responses by human CCR3+ endothelial cells. J. Immunol. 166:7571
11. R. B. Kodali, W. J. Kim and I. I. Galaria et al., CCL11 (eotaxin) induces CCR3-dependent smooth muscle cell migration, Arterioscler Thromb Vasc Biol 24 (2004), pp. 1211-1216.
12. Forssmann U. et al. Eotaxin-2, a novel CC chemokine that is selective for the chemokine receptor CCR3, and acts like eotaxin on human eosinophil and basophil leukocytes J. Exp. Med. 1997; 185:2171-2176
13. Romagnani P A F, Lasagni L, Lazzeri E, Beltrame C, Francalanci M, Uguccioni M, Galli G, Cosmi L, Maurenzig L, Baggiolini M, Maggi E, Romagnani S, Serio M. Cell cycle-dependent expression of CXC chemokine receptor 3 by endothelial cells mediates angiostatic activity. J Clin Invest 2001; 107(1):53-63.
14. Garcia G G V, Humbert M. New chemokine targets for asthma therapy. Curr Allergy Asthma Rep 2005; 5(2):155-60.
15. Zimmerman N P V R, Wendt M K, Dwinell M B. Chemokines and chemokine receptors in mucosal homeostasis at the intestinal epithelial barrier in inflammatory bowel disease. Inflamm Bowel Dis 2008; 14(7):1000-11.
16. Simpson J R P, Newcombe J, Cuzner M L, Male D, Woodroofe M N. Expression of the beta-chemokine receptors CCR2, CCR3 and CCR5 in multiple sclerosis central nervous system tissue. J Neuroimmunol 2000; 108(1-2): 192-200.

17. Firestein G S. Evolving concepts of rheumatoid arthritis. Nature 2003; 423(6937):356-6.
18. Arend W P. Physiology of cytokine pathways in rheumatoid arthritis. Arthritis Rheum 2001; 45(1):101-6.
19. Guglielmotti A DOE, Coletta I, Aquilini L, Milanese C, Pinza M. Amelioration of rat adjuvant arthritis by therapeutic treatment with bindarit, an inhibitor of MCP-1 and TNF-alpha production. Inflamm Res 2002; 51(5):252-8.
20. Haas C S M R, Attia N, Haines G K 3rd, Campbell P L, Koch A E. Chemokine receptor expression in rat adjuvant-induced arthritis. Arthritis Rheum 2005; 52(12):3718-30.
21. Haringman J J S T, Reinders-Blankert P, Tak P P. Chemokine and chemokine receptor expression in paired peripheral blood mononuclear cells and synovial tissue of patients with rheumatoid arthritis, osteoarthritis, and reactive arthritis. Ann Rheum Dis 2006; 65(3):294-300.
22. Charo I F, Taubman M B. Chemokines in the pathogenesis of vascular disease. Circ Res. 2004; 95: 858-66.
23. Sheikine S, Hansson G K. Chemokines as potential therapeutic targets in atherosclerosis, Curr Drug Targets 2006; 7: 13-28.
24. Haley K J, Lilly C M, Yang J H, et al., Overexpression of eotaxin and the CCR3 receptor in human atherosclerosis: using genomic technology to identify a potential novel pathway of vascular inflammation, Circulation 2000; 102: 2185-2189.
25. Sheikine Y, Olsen B, Gharizadeh B, Jatta K, Tornvall P, Ghaderi M. Influence of eotaxin 67G>A polymorphism on plasma eotaxin concentrations in myocardial infarction survivors and healthy controls. Atherosclerosis. 2006; 189: 458-63.
26. Emanuele E, Falcone C, D'Angelo A, Minoretti P, Buzzi M P, Bertona M, Geroldi D. Association of plasma eotaxin levels with the presence and extent of angiographic coronary artery disease. Atherosclerosis. 2006 May; 186(1): 140-5.
27. E. Economou, D. Tousoulis and A. Katinioti et al., Chemokines in patients with ischaemic heart disease and the effect of coronary angioplasty, Int J Cardiol 80 (2001), pp. 55-60.
28. Naghavi M, et al. From vulnerable plaque to vulnerable patient: a call for new definitions and risk assessment strategies: Part I. Circulation. 2003; 108: 1664-72.
29. Naghavi M, et al. From vulnerable plaque to vulnerable patient: a call for new definitions and risk assessment strategies: Part II. Circulation. 2003; 108: 1772-8.
30. Mendel I et al. Eur J Immunol 1995 25:1951-9
31. Zargari M et al. Neurosci Lett. 2007. 412: 24-8
32. Delovitch T L, and Singh B. Immunity 1997 Dec.; 7(6): 727-38.
33. George J, Afek A, Gilburd B, Aron-Maor A Shaish A, Levkovitz H, Blank M, Harats D, Shoenfeld Y. Induction of early atherosclerosis in LDL receptor deficient mice immunized with beta 2 glycoproein I. Circulation. 1998; 15: 1108-1115.

TABLE 1

| Accession no. | Product size | primers | mRNA target |
|---|---|---|---|
| AF281075 | 379 bp | CTGTGCCTGACCTC CAGAAC (SEQ ID NO. 12) CTAAACCTCGGTGC TATTGC (SEQ ID NO. 13) | Eotaxin-2 |
| NM_011577 | 492 bp | CTTGGGCTTGCGAC CCACGTAGTA (SEQ ID NO. 14) AGACGGAATACAGG GCTTTCGATTCA (SEQ ID NO. 15) | TGFbeta |
| NM_199472 | 585 bp | AGCCCATCACCATC TTCCAG (SEQ ID NO. 16) CCTGCTTCACCACC TTCTTG (SEQ ID NO. 17) | G3PDH |

The invention claimed is:

1. A method of treating an inflammatory or autoimmune disease, comprising:
   administering to a patient in need thereof, a therapeutically effective amount of a pharmaceutical composition comprising an anti eotaxin 2 monoclonal antibody comprising a heavy chain encoded by a nucleic acid having at least 90% homology with SEQ ID NO:1 and a light chain encoded by a nucleic acid having at least 90% homology with SEQ ID NO:2, or a fragment thereof which retains the binding activity of the antibody.

2. The method according to claim 1, wherein the pharmaceutical composition is administered in combination with at least one additional therapeutic agent.

3. The method according to claim 2, wherein the at least one additional therapeutic agent is cyclosporine.

4. The method according to claim 2, wherein the at least one additional therapeutic agent is methotrexate.

5. The method according to claim 2, wherein the at least one additional therapeutic agent is an anti-TNFα antibody.

6. The method according to claim 2, wherein the at least one additional therapeutic agent an anti-TNF receptor antibody.

7. The method according to claim 2, wherein the at least one additional therapeutic agent is an anti-IL6 receptor antibody.

8. The method according to claim 2, wherein the at least one additional therapeutic agent is an anti-CD20 antibody.

9. The method according to claim 2, wherein the at least one additional therapeutic agent is an anti-VLA-4 antibody.

10. The method according to claim 2, wherein the at least one additional therapeutic agent is an intravenous immune globulin (IVIG).

11. The method according to claim 2, wherein the at least one additional therapeutic agent is copaxone.

12. The method according to claim 2, wherein the at least one additional therapeutic agent is interferon-β.

13. A method of treating an inflammatory or autoimmune disease, comprising:
    administering to a patient in need thereof, a therapeutically effective amount of a pharmaceutical composition comprising an anti eotaxin 2 monoclonal antibody secreted by hybridoma D8 (ECACC Accession No. D809081702) or a fragment thereof which retains the binding activity of the antibody.

14. The method according to claim 13, wherein the pharmaceutical composition is administered in combination with at least one additional therapeutic agent.

15. The method according to claim 14, wherein the at least one additional therapeutic agent is methotrexate.

16. A method of treating an inflammatory or autoimmune disease, comprising:
    administering to a patient in need thereof, a therapeutically effective amount of a pharmaceutical composition comprising an anti eotaxin 2 monoclonal antibody comprising a heavy chain encoded by a nucleic acid having at least 90% homology with the nucleic acid encoding the heavy chain of the monoclonal antibody secreted by hybridoma D8 (ECACC Accession No. D809081702) and a light chain encoded by a nucleic acid having at least 90% homology with the nucleic acid encoding the light chain of the monoclonal antibody secreted by hybridoma D8 (ECACC Accession No. D809081702), or a fragment thereof which retains the binding activity of the antibody.

17. The method according to claim 16, wherein the pharmaceutical composition is administered in combination with at least one additional therapeutic agent.

18. The method according to claim 17, wherein the at least one additional therapeutic agent is methotrexate.

* * * * *